(12) United States Patent
Mosnier et al.

(10) Patent No.: US 10,918,422 B2
(45) Date of Patent: Feb. 16, 2021

(54) METHOD AND APPARATUS FOR INHIBITING PROXIMAL JUNCTIONAL FAILURE

(71) Applicant: Medicrea International, Rillieux-la-Pape (FR)

(72) Inventors: Thomas Mosnier, Rochetaillée sur Saône (FR); David Nicholas Ryan, Collonges au Mont d'Or (FR)

(73) Assignee: Medicrea International, Rillieux-la-Pape (FR)

( * ) Notice: Subject to any disclaimer, the term of this patent is extended or adjusted under 35 U.S.C. 154(b) by 57 days.

(21) Appl. No.: 16/206,590

(22) Filed: Nov. 30, 2018

(65) Prior Publication Data
US 2019/0167314 A1   Jun. 6, 2019

Related U.S. Application Data

(60) Provisional application No. 62/593,570, filed on Dec. 1, 2017.

(51) Int. Cl.
*A61B 17/70* (2006.01)
*A61B 17/16* (2006.01)
*A61B 17/84* (2006.01)
*A61B 17/82* (2006.01)

(52) U.S. Cl.
CPC ...... *A61B 17/7053* (2013.01); *A61B 17/1606* (2013.01); *A61B 17/7001* (2013.01); *A61B 17/707* (2013.01); *A61B 17/7049* (2013.01); *A61B 17/7062* (2013.01); *A61B 17/7076* (2013.01); *A61B 17/82* (2013.01); *A61B 17/842* (2013.01)

(58) Field of Classification Search
CPC . A61B 17/7053; A61B 17/7049; A61B 17/82; A61B 17/842
See application file for complete search history.

(56) References Cited

U.S. PATENT DOCUMENTS

| | | | |
|---|---|---|---|
| 4,382,438 A | 5/1983 | Jacobs | |
| 5,006,984 A | 4/1991 | Steele | |
| 5,011,484 A * | 4/1991 | Breard | A61B 17/7053 |
| | | | 606/249 |
| 5,163,440 A | 11/1992 | DeLuca et al. | |

(Continued)

FOREIGN PATENT DOCUMENTS

| | | |
|---|---|---|
| AU | 2015258176 | 12/2015 |
| AU | 2015202416 | 3/2017 |

(Continued)

OTHER PUBLICATIONS

US 9,451,972 B2, 09/2016, Lang et al. (withdrawn)

(Continued)

*Primary Examiner* — Nicholas J Plionis

(57) ABSTRACT

Methods and devices are disclosed for inhibiting proximal junctional failure in a patient having posterior spinal instrumentation. One or more tension bands can be threaded through transverse bores in a spinous process of a vertebral body of a spine, superior and adjacent an uppermost instrumented vertebral body. Tension is applied to bias the spinous processes together and also in an inferior direction. The tension band is locked with respect to the spine, to maintain tension.

13 Claims, 19 Drawing Sheets

(56) References Cited

U.S. PATENT DOCUMENTS

| | | | |
|---|---|---|---|
| 5,209,752 | A | 5/1993 | Ashman et al. |
| 5,224,035 | A | 6/1993 | Yamashita et al. |
| 5,251,127 | A | 10/1993 | Raab |
| 5,291,901 | A | 3/1994 | Graf |
| 5,305,203 | A | 4/1994 | Raab |
| 5,312,405 | A | 5/1994 | Korotko et al. |
| 5,366,455 | A * | 11/1994 | Dove ............... A61B 17/7053 606/250 |
| 5,413,116 | A | 5/1995 | Radke et al. |
| 5,514,180 | A | 5/1996 | Heggeness |
| 5,609,634 | A * | 3/1997 | Voydeville ......... A61B 17/7062 606/248 |
| 5,667,506 | A | 9/1997 | Sutterlin |
| 5,748,767 | A | 5/1998 | Raab |
| 5,785,663 | A | 7/1998 | Sarvazyan |
| 6,015,409 | A | 1/2000 | Jackson |
| 6,086,590 | A * | 7/2000 | Margulies ............ A61B 17/842 606/263 |
| 6,213,958 | B1 | 4/2001 | Winder |
| 6,277,120 | B1 * | 8/2001 | Lawson ............. A61B 17/7053 606/263 |
| 6,282,437 | B1 | 8/2001 | Franck et al. |
| 6,302,888 | B1 | 10/2001 | Mellinger et al. |
| 6,364,849 | B1 | 4/2002 | Wilcox |
| 6,385,475 | B1 | 5/2002 | Cinquin et al. |
| 6,409,684 | B1 | 6/2002 | Wilk |
| 6,443,953 | B1 | 9/2002 | Perra et al. |
| 6,499,488 | B1 | 12/2002 | Hunter et al. |
| 6,565,519 | B2 | 5/2003 | Benesh |
| 6,585,666 | B2 | 7/2003 | Suh et al. |
| 6,711,432 | B1 | 3/2004 | Krause et al. |
| 6,715,213 | B2 | 4/2004 | Richter |
| 6,716,213 | B2 | 4/2004 | Shitoto |
| 6,746,449 | B2 | 6/2004 | Jones et al. |
| 6,786,930 | B2 | 9/2004 | Biscup |
| 7,066,938 | B2 | 6/2006 | Slivka et al. |
| 7,338,526 | B2 | 3/2008 | Steinberg et al. |
| 7,509,183 | B2 | 3/2009 | Lin |
| 7,534,263 | B2 | 5/2009 | Burdulis |
| 7,542,791 | B2 | 6/2009 | Mire et al. |
| 7,570,791 | B2 | 8/2009 | Frank et al. |
| 7,606,613 | B2 | 10/2009 | Simon et al. |
| 7,611,522 | B2 | 11/2009 | Gorek |
| 7,618,451 | B2 | 11/2009 | Fitz et al. |
| 7,634,119 | B2 | 12/2009 | Tsougarakis et al. |
| 7,635,367 | B2 | 12/2009 | Groiso |
| 7,639,866 | B2 | 12/2009 | Pomero et al. |
| 7,660,623 | B2 | 2/2010 | Hunter et al. |
| 7,674,293 | B2 | 3/2010 | Kuiper et al. |
| 7,715,602 | B2 | 5/2010 | Richard |
| 7,763,054 | B2 | 7/2010 | Clement et al. |
| 7,824,413 | B2 | 11/2010 | Varieur et al. |
| 7,835,778 | B2 | 11/2010 | Foley et al. |
| 7,840,253 | B2 | 11/2010 | Tremblay et al. |
| 7,862,593 | B2 | 1/2011 | Clement et al. |
| 7,918,887 | B2 | 4/2011 | Roche |
| 7,953,471 | B2 | 5/2011 | Clayton et al. |
| 7,974,677 | B2 | 7/2011 | Mire et al. |
| 7,981,158 | B2 | 7/2011 | Fitz et al. |
| 7,996,061 | B2 | 8/2011 | Mollard et al. |
| 7,996,064 | B2 | 8/2011 | Simon et al. |
| 8,000,926 | B2 | 8/2011 | Roche et al. |
| 8,036,441 | B2 | 10/2011 | Frank et al. |
| 8,038,716 | B2 | 10/2011 | Duggal et al. |
| 8,046,050 | B2 | 10/2011 | Govari et al. |
| 8,066,708 | B2 | 11/2011 | Lang et al. |
| 8,077,950 | B2 | 12/2011 | Tsougarakis et al. |
| 8,083,778 | B2 | 12/2011 | Clement et al. |
| 8,105,330 | B2 | 1/2012 | Fitz et al. |
| 8,142,842 | B2 | 3/2012 | Nicholas et al. |
| 8,196,825 | B2 | 6/2012 | Turner et al. |
| 8,211,109 | B2 | 7/2012 | Groiso |
| 8,211,153 | B2 | 7/2012 | Shaolian et al. |
| 8,234,097 | B2 | 7/2012 | Steines et al. |
| 8,241,296 | B2 | 8/2012 | Wasielewski |
| 8,246,680 | B2 | 8/2012 | Betz et al. |
| 8,265,790 | B2 | 9/2012 | Amiot et al. |
| 8,270,253 | B1 | 9/2012 | Roche et al. |
| 8,275,594 | B2 | 9/2012 | Lin et al. |
| 8,308,772 | B2 | 11/2012 | Clement et al. |
| 8,308,775 | B2 | 11/2012 | Clement et al. |
| 8,337,501 | B2 | 12/2012 | Fitz et al. |
| 8,357,111 | B2 | 1/2013 | Caillouette et al. |
| 8,357,166 | B2 | 1/2013 | Aram et al. |
| 8,372,075 | B2 | 2/2013 | Groiso |
| 8,377,073 | B2 | 2/2013 | Wasielewski |
| 8,394,142 | B2 | 3/2013 | Berg et al. |
| 8,398,681 | B2 | 3/2013 | Augostino et al. |
| 8,400,312 | B2 | 3/2013 | Hotokebuchi et al. |
| 8,414,592 | B2 | 4/2013 | Quirno |
| 8,442,621 | B2 | 5/2013 | Gorek et al. |
| 8,457,930 | B2 | 6/2013 | Schroeder |
| 8,465,527 | B2 | 6/2013 | Clement |
| 8,494,805 | B2 | 7/2013 | Roche et al. |
| 8,506,632 | B2 | 8/2013 | Ganem et al. |
| 8,532,806 | B1 | 9/2013 | Masson |
| 8,535,337 | B2 | 9/2013 | Chang et al. |
| 8,549,888 | B2 | 10/2013 | Isaacs |
| 8,556,983 | B2 | 10/2013 | Bojarski et al. |
| 8,562,653 | B2 * | 10/2013 | Alamin ............... A61B 17/7067 606/279 |
| 8,588,892 | B2 | 11/2013 | Hladio et al. |
| 8,636,776 | B2 | 1/2014 | Rosenberg et al. |
| 8,672,948 | B2 | 3/2014 | Lemaitre |
| 8,685,093 | B2 | 4/2014 | Anderson et al. |
| 8,690,888 | B2 | 4/2014 | Stein et al. |
| 8,705,829 | B2 | 4/2014 | Frank et al. |
| 8,718,820 | B2 | 5/2014 | Amiot et al. |
| 8,740,941 | B2 * | 6/2014 | Thramann ............... A61B 17/70 606/246 |
| 8,758,357 | B2 | 6/2014 | Frey |
| 8,775,133 | B2 | 7/2014 | Schroeder |
| 8,777,877 | B2 | 7/2014 | Stein et al. |
| 8,784,339 | B2 | 7/2014 | Stein et al. |
| 8,801,786 | B2 | 8/2014 | Bernard et al. |
| 8,814,877 | B2 | 8/2014 | Wasielewski |
| 8,814,915 | B2 | 8/2014 | Hess et al. |
| 8,845,689 | B2 * | 9/2014 | Douget ............... A61B 17/7055 606/249 |
| 8,852,237 | B2 | 10/2014 | Kalfas et al. |
| 8,855,389 | B1 | 10/2014 | Hoffman et al. |
| 8,864,764 | B2 | 10/2014 | Groiso |
| 8,870,889 | B2 | 10/2014 | Frey |
| 8,900,316 | B2 | 12/2014 | Lenz |
| 8,911,448 | B2 | 12/2014 | Stein |
| 8,926,673 | B2 | 1/2015 | Clement et al. |
| 8,945,133 | B2 | 2/2015 | Stein et al. |
| 8,956,416 | B2 | 2/2015 | McCarthy |
| 8,974,467 | B2 | 3/2015 | Stone |
| 8,983,813 | B2 | 3/2015 | Miles et al. |
| 8,998,962 | B2 | 4/2015 | Birch |
| 9,011,448 | B2 | 4/2015 | Roche et al. |
| 9,034,037 | B2 | 5/2015 | Fiere et al. |
| 9,039,772 | B2 | 5/2015 | Park et al. |
| 9,056,017 | B2 | 6/2015 | Kotlus |
| 9,066,701 | B1 | 6/2015 | Finley et al. |
| 9,066,734 | B2 | 6/2015 | Schoenfeld et al. |
| 9,078,755 | B2 | 7/2015 | Mahfouz |
| 9,101,492 | B2 | 8/2015 | Mangione et al. |
| 9,107,706 | B2 * | 8/2015 | Alamin ............... A61B 17/7064 |
| 9,115,998 | B2 | 8/2015 | Proulx et al. |
| 9,119,572 | B2 | 9/2015 | Gorek et al. |
| 9,119,671 | B2 | 9/2015 | Kast |
| 9,125,680 | B2 | 9/2015 | Kostrzewski et al. |
| 9,144,440 | B2 | 9/2015 | Aminian |
| 9,144,470 | B2 | 9/2015 | Proulx et al. |
| 9,168,153 | B2 | 10/2015 | Bettenga |
| 9,173,661 | B2 | 11/2015 | Metzger et al. |
| 9,180,015 | B2 | 11/2015 | Fitz et al. |
| 9,192,412 | B2 | 11/2015 | Meyrat et al. |
| 9,198,678 | B2 | 12/2015 | Frey et al. |
| 9,232,955 | B2 | 1/2016 | Bonin, Jr. et al. |
| 9,233,001 | B2 | 1/2016 | Miles et al. |
| 9,237,952 | B2 | 1/2016 | Kurtz |

(56) References Cited

U.S. PATENT DOCUMENTS

| | | |
|---|---|---|
| 9,248,023 B2 | 2/2016 | Ries et al. |
| 9,250,620 B2 | 2/2016 | Kotlus |
| 9,278,010 B2 | 3/2016 | Gibson et al. |
| 9,283,048 B2 | 3/2016 | Kostrzewski et al. |
| 9,289,221 B2 | 3/2016 | Gelaude et al. |
| 9,289,270 B2 | 3/2016 | Gielen et al. |
| 9,295,482 B2 | 3/2016 | Fitz et al. |
| 9,295,497 B2 | 3/2016 | Schoenfeld et al. |
| 9,295,561 B2 | 3/2016 | Ball et al. |
| 9,301,768 B2 | 4/2016 | Buza et al. |
| 9,308,050 B2 | 4/2016 | Kostrzewski et al. |
| 9,308,091 B2 | 4/2016 | Lang |
| 9,314,275 B2 | 4/2016 | Clement et al. |
| 9,314,343 B2 | 4/2016 | Parisi et al. |
| 9,320,547 B2 | 4/2016 | Augostino |
| 9,320,604 B2 | 4/2016 | Miles et al. |
| 9,326,780 B2 | 5/2016 | Wong et al. |
| 9,339,277 B2 | 5/2016 | Jansen et al. |
| 9,345,492 B2 | 5/2016 | Stein et al. |
| 9,358,051 B2 | 6/2016 | Sournac et al. |
| 9,358,130 B2 | 6/2016 | Livorsi et al. |
| 9,358,136 B2 | 6/2016 | Stein et al. |
| 9,364,370 B2 | 6/2016 | Kühnel |
| 9,381,085 B2 | 7/2016 | Axelson et al. |
| 9,387,015 B2 | 7/2016 | Taylor |
| 9,392,953 B1 | 7/2016 | Gharib |
| 9,393,052 B2 | 7/2016 | Berg et al. |
| 9,398,962 B2 | 7/2016 | Steinberg |
| 9,402,726 B2 | 8/2016 | Linderman et al. |
| 9,408,615 B2 | 8/2016 | Fitz et al. |
| 9,408,642 B2 | 8/2016 | Wong et al. |
| 9,408,698 B2 | 8/2016 | Miles et al. |
| 9,414,940 B2 | 8/2016 | Stein et al. |
| 9,433,443 B2 | 9/2016 | Montello et al. |
| 9,439,659 B2 | 9/2016 | Schoenefeld et al. |
| 9,439,767 B2 | 9/2016 | Bojarski et al. |
| 9,439,781 B2 | 9/2016 | Gibson |
| 9,445,913 B2 | 9/2016 | Donner et al. |
| 9,452,022 B2 | 9/2016 | McIntosh et al. |
| 9,452,023 B2 | 9/2016 | Boillot et al. |
| 9,452,050 B2 | 9/2016 | Miles et al. |
| 9,452,064 B2 | 9/2016 | Trautwein et al. |
| 9,468,436 B2 | 10/2016 | Groiso |
| 9,468,502 B2 | 10/2016 | Wiebe et al. |
| 9,491,415 B2 | 11/2016 | Deitz et al. |
| 9,492,183 B2 | 11/2016 | Wilkinson et al. |
| 9,495,483 B2 | 11/2016 | Steines et al. |
| 9,495,509 B2 | 11/2016 | Amiot et al. |
| 9,498,260 B2 | 11/2016 | Funk et al. |
| 9,504,502 B2 | 11/2016 | Kuiper et al. |
| 9,510,771 B1 | 12/2016 | Finley et al. |
| 9,510,864 B2 | 12/2016 | Devito |
| 9,517,134 B2 | 12/2016 | Lang |
| 9,517,143 B2 | 12/2016 | Prevost et al. |
| 9,526,514 B2 | 12/2016 | Kelley et al. |
| 9,532,730 B2 | 1/2017 | Wasielewski |
| 9,539,031 B2 | 1/2017 | Fauth |
| 9,539,116 B2 | 1/2017 | Claypool et al. |
| 9,539,760 B2 | 1/2017 | Stahl et al. |
| 9,547,897 B2 | 1/2017 | Parent et al. |
| 9,549,782 B2 | 1/2017 | Park et al. |
| 9,554,411 B1 | 1/2017 | Hall et al. |
| 9,554,910 B2 | 1/2017 | Vanasse et al. |
| 9,561,115 B2 | 2/2017 | Elahinia et al. |
| 9,566,075 B2 | 2/2017 | Carroll |
| 9,579,043 B2 | 2/2017 | Chien et al. |
| 9,585,597 B2 | 3/2017 | McCaullet et al. |
| 9,597,096 B2 | 3/2017 | Aghazadeh |
| 9,597,156 B2 | 3/2017 | Amiot et al. |
| 9,603,613 B2 | 3/2017 | Schoenefeld et al. |
| 9,603,623 B2 | 3/2017 | Brooks et al. |
| 9,603,711 B2 | 3/2017 | Bojarski et al. |
| 9,610,086 B2 | 4/2017 | Park et al. |
| 9,615,834 B2 | 4/2017 | Agmihotri et al. |
| 9,622,712 B2 | 4/2017 | Munro et al. |
| 9,629,723 B2 | 4/2017 | Parisi et al. |
| 9,636,181 B2 | 5/2017 | Isaacs |
| 9,642,633 B2 | 5/2017 | Frey et al. |
| 9,649,170 B2 | 5/2017 | Park et al. |
| 9,655,729 B2 | 5/2017 | Parisi et al. |
| 9,662,214 B2 | 5/2017 | Li et al. |
| 9,668,748 B2 | 6/2017 | McKinnon et al. |
| 9,668,873 B2 | 6/2017 | Winslow |
| 9,675,471 B2 | 6/2017 | Bojarski et al. |
| 9,693,831 B2 | 7/2017 | Mosnier |
| 9,715,563 B1 | 7/2017 | Schroeder |
| 9,757,072 B1 | 9/2017 | Urbalejo |
| 9,782,228 B2 | 10/2017 | Mosnier et al. |
| 9,788,966 B2 | 10/2017 | Steinberg |
| 9,827,109 B2 | 11/2017 | Steinberg |
| 9,848,922 B2 | 12/2017 | Tohmeh et al. |
| 9,968,408 B1 | 5/2018 | Casey et al. |
| 9,987,048 B2 | 6/2018 | Mosnier et al. |
| 9,993,177 B2 | 6/2018 | Chien et al. |
| 10,010,426 B2 | 7/2018 | Kuiper et al. |
| 10,045,824 B2 | 8/2018 | Mosnier et al. |
| 10,052,135 B2 | 8/2018 | Berg et al. |
| 10,064,656 B2 * | 9/2018 | Mundis, Jr. ......... A61B 17/701 |
| 10,064,743 B2 | 9/2018 | Funk et al. |
| 10,098,671 B2 | 10/2018 | Augostino |
| 10,188,480 B2 | 1/2019 | Scholl et al. |
| 10,201,320 B2 | 2/2019 | Saget |
| 10,219,865 B2 | 3/2019 | Jansen |
| 10,292,770 B2 | 5/2019 | Ryan et al. |
| 10,314,657 B2 | 6/2019 | Mosnier et al. |
| 10,318,655 B2 | 6/2019 | Mosnier |
| 10,413,365 B1 | 9/2019 | Mosnier et al. |
| 10,420,615 B1 | 9/2019 | Mosnier et al. |
| 10,433,893 B1 | 10/2019 | Scholl et al. |
| 10,433,912 B1 | 10/2019 | Mosnier et al. |
| 10,433,913 B2 | 10/2019 | Mosnier et al. |
| 10,441,363 B1 | 10/2019 | Mosnier et al. |
| 10,456,174 B2 * | 10/2019 | Mickiewicz ....... A61B 17/7043 |
| 10,456,211 B2 | 10/2019 | Mosnier et al. |
| 10,463,433 B2 | 11/2019 | Turner et al. |
| 2002/0035321 A1 | 3/2002 | Bucholz et al. |
| 2002/0038118 A1 | 3/2002 | Shoham |
| 2002/0045812 A1 | 4/2002 | Ben-Haim et al. |
| 2002/0068936 A1 | 6/2002 | Burkus |
| 2002/0103432 A1 | 8/2002 | Kawchuk |
| 2003/0191383 A1 | 10/2003 | Ben-Haim et al. |
| 2003/0204189 A1 | 10/2003 | O'Neil et al. |
| 2004/0120781 A1 | 6/2004 | Luca |
| 2004/0143243 A1 | 7/2004 | Wahrburg |
| 2004/0152972 A1 | 8/2004 | Hunter |
| 2004/0167637 A1 | 8/2004 | Biscup |
| 2004/0171924 A1 | 9/2004 | Mire |
| 2004/0172020 A1 | 9/2004 | Beaurain et al. |
| 2004/0215190 A1 | 10/2004 | Nguyen et al. |
| 2004/0243148 A1 | 12/2004 | Wasuekewski |
| 2004/0267279 A1 | 12/2004 | Casutt et al. |
| 2005/0149050 A1 | 7/2005 | Stifter et al. |
| 2005/0177239 A1 | 8/2005 | Steinberg |
| 2005/0182320 A1 | 8/2005 | Stifter et al. |
| 2005/0182454 A1 | 8/2005 | Kaula et al. |
| 2005/0203531 A1 | 9/2005 | Lakin et al. |
| 2005/0203532 A1 | 9/2005 | Ferguson et al. |
| 2005/0262911 A1 | 12/2005 | Dankowicz et al. |
| 2006/0015018 A1 | 1/2006 | Jutras et al. |
| 2006/0015030 A1 | 1/2006 | Poulin et al. |
| 2006/0036259 A1 | 2/2006 | Carl |
| 2006/0069324 A1 | 3/2006 | Block et al. |
| 2006/0074431 A1 | 4/2006 | Sutton et al. |
| 2006/0136058 A1 | 6/2006 | Pietrzak |
| 2006/0142657 A1 | 6/2006 | Quaid |
| 2006/0285991 A1 | 12/2006 | McKinley |
| 2006/0287627 A1 | 12/2006 | Johnson |
| 2007/0021682 A1 | 1/2007 | Gharib et al. |
| 2007/0118243 A1 | 5/2007 | Schroeder et al. |
| 2007/0173818 A1 * | 7/2007 | Hestad ............... A61B 17/7062 606/279 |
| 2007/0225731 A1 | 9/2007 | Couture et al. |
| 2008/0009866 A1 * | 1/2008 | Alamin ............ A61B 17/7067 606/249 |

(56) References Cited

U.S. PATENT DOCUMENTS

| | | | |
|---|---|---|---|
| 2008/0058945 A1 | 3/2008 | Hajaj et al. | |
| 2008/0108991 A1 | 5/2008 | von Jako | |
| 2008/0177203 A1 | 7/2008 | von Jako | |
| 2008/0255575 A1 | 10/2008 | Justis et al. | |
| 2008/0262549 A1* | 10/2008 | Bennett | A61B 17/7062 606/263 |
| 2008/0281332 A1 | 11/2008 | Taylor | |
| 2009/0024164 A1 | 1/2009 | Neubardt | |
| 2009/0076615 A1 | 3/2009 | Duggal et al. | |
| 2009/0157083 A1 | 6/2009 | Park et al. | |
| 2009/0194206 A1 | 8/2009 | Jeon et al. | |
| 2009/0204159 A1 | 8/2009 | Justis et al. | |
| 2009/0248080 A1 | 8/2009 | Justis et al. | |
| 2009/0249851 A1 | 10/2009 | Isaacs | |
| 2009/0254326 A1 | 10/2009 | Isaacs | |
| 2009/0264932 A1* | 10/2009 | Alamin | A61B 17/7053 606/263 |
| 2010/0042157 A1 | 2/2010 | Trieu | |
| 2010/0100011 A1 | 4/2010 | Roche | |
| 2010/0191071 A1 | 7/2010 | Anderson et al. | |
| 2010/0191088 A1 | 7/2010 | Anderson | |
| 2010/0217270 A1 | 8/2010 | Polinski et al. | |
| 2010/0217336 A1 | 8/2010 | Crawford et al. | |
| 2011/0004309 A9 | 3/2011 | Bojarski et al. | |
| 2011/0071802 A1 | 3/2011 | Bojarski et al. | |
| 2011/0106163 A1* | 5/2011 | Hochschuler | A61B 17/7071 606/264 |
| 2011/0118740 A1 | 5/2011 | Rabiner et al. | |
| 2011/0137345 A1* | 6/2011 | Stoll | A61B 17/7083 606/251 |
| 2011/0172566 A1 | 7/2011 | Kawchuk | |
| 2011/0214279 A1 | 9/2011 | Park et al. | |
| 2011/0224796 A1 | 9/2011 | Weiland et al. | |
| 2011/0257653 A1 | 10/2011 | Hughes et al. | |
| 2011/0257657 A1 | 10/2011 | Turner et al. | |
| 2011/0295159 A1 | 12/2011 | Shachar et al. | |
| 2011/0295378 A1 | 12/2011 | Bojarski et al. | |
| 2011/0306873 A1 | 12/2011 | Shenai et al. | |
| 2012/0022357 A1 | 1/2012 | Chang et al. | |
| 2012/0027261 A1 | 2/2012 | Frank et al. | |
| 2012/0035611 A1 | 2/2012 | Kave | |
| 2012/0123301 A1 | 5/2012 | Connor et al. | |
| 2012/0143090 A1 | 6/2012 | Hay et al. | |
| 2012/0150243 A9 | 6/2012 | Crawford et al. | |
| 2012/0165872 A1* | 6/2012 | Alamin | A61B 17/7062 606/248 |
| 2012/0172884 A1 | 7/2012 | Zheng et al. | |
| 2012/0203289 A1 | 8/2012 | Beerens et al. | |
| 2013/0079678 A1 | 3/2013 | Stein et al. | |
| 2013/0079679 A1 | 3/2013 | Roche et al. | |
| 2013/0079790 A1 | 3/2013 | Stein et al. | |
| 2013/0131486 A1 | 5/2013 | Copf et al. | |
| 2013/0345718 A1 | 6/2013 | Crawford et al. | |
| 2013/0211531 A1 | 8/2013 | Steines et al. | |
| 2013/0245631 A1 | 9/2013 | Bettenga | |
| 2013/0253599 A1 | 9/2013 | Gorek et al. | |
| 2013/0268007 A1 | 10/2013 | Rezach et al. | |
| 2013/0303883 A1 | 11/2013 | Zehavi et al. | |
| 2014/0058407 A1 | 2/2014 | Tsekos | |
| 2014/0100579 A1 | 4/2014 | Kelman et al. | |
| 2014/0135658 A1 | 5/2014 | Hladio et al. | |
| 2014/0180415 A1 | 6/2014 | Koss | |
| 2014/0194889 A1 | 7/2014 | Chang et al. | |
| 2014/0228670 A1 | 8/2014 | Justis et al. | |
| 2014/0228860 A1 | 8/2014 | Steines et al. | |
| 2014/0244220 A1 | 8/2014 | McKinnon et al. | |
| 2014/0257402 A1 | 9/2014 | Barsoum | |
| 2014/0272881 A1 | 9/2014 | Barsoum | |
| 2014/0277149 A1 | 9/2014 | Rooney | |
| 2014/0296860 A1 | 10/2014 | Stein et al. | |
| 2014/0303672 A1 | 10/2014 | Tran et al. | |
| 2014/0316468 A1 | 10/2014 | Keiser et al. | |
| 2015/0057756 A1 | 2/2015 | Lang et al. | |
| 2015/0066145 A1 | 3/2015 | Rogers et al. | |
| 2015/0080901 A1 | 3/2015 | Stein | |
| 2015/0081029 A1 | 3/2015 | Bojarski et al. | |
| 2015/0088030 A1 | 3/2015 | Gharib et al. | |
| 2015/0100066 A1 | 4/2015 | Kostrezewski et al. | |
| 2015/0100091 A1 | 4/2015 | Tohmeh et al. | |
| 2015/0105782 A1 | 4/2015 | D'Lima et al. | |
| 2015/0127055 A1 | 5/2015 | Dvorak et al. | |
| 2015/0150646 A1 | 6/2015 | Pryor et al. | |
| 2015/0164657 A1 | 6/2015 | Miles et al. | |
| 2015/0182292 A1 | 7/2015 | Hladio et al. | |
| 2015/0223900 A1 | 8/2015 | Wiebe et al. | |
| 2015/0245844 A1 | 9/2015 | Kennedy et al. | |
| 2015/0250597 A1 | 9/2015 | Lang et al. | |
| 2015/0265291 A1 | 9/2015 | Wilkinson | |
| 2015/0305878 A1 | 10/2015 | O'Neil et al. | |
| 2015/0305891 A1 | 10/2015 | Bergin et al. | |
| 2015/0313723 A1 | 11/2015 | Jansen et al. | |
| 2015/0328004 A1 | 11/2015 | Mahfouz | |
| 2015/0366630 A1 | 12/2015 | Gorek et al. | |
| 2016/0000571 A1 | 1/2016 | Mahfouz | |
| 2016/0007983 A1 | 1/2016 | Frey et al. | |
| 2016/0015465 A1 | 1/2016 | Steines et al. | |
| 2016/0022176 A1 | 1/2016 | Le Huec et al. | |
| 2016/0022370 A1 | 1/2016 | Pavlovskaia et al. | |
| 2016/0038161 A1 | 2/2016 | Gibson | |
| 2016/0038238 A1 | 2/2016 | Kostrzewski et al. | |
| 2016/0038242 A1 | 2/2016 | Lo Iacono et al. | |
| 2016/0038293 A1 | 2/2016 | Slamin et al. | |
| 2016/0038307 A1 | 2/2016 | Bettenga | |
| 2016/0045230 A1 | 2/2016 | Lowery et al. | |
| 2016/0045317 A1 | 2/2016 | Lang et al. | |
| 2016/0045326 A1 | 2/2016 | Hansen et al. | |
| 2016/0058320 A1 | 3/2016 | Chien et al. | |
| 2016/0058523 A1 | 3/2016 | Chien et al. | |
| 2016/0074052 A1 | 3/2016 | Keppler et al. | |
| 2016/0074202 A1 | 3/2016 | Reed et al. | |
| 2016/0081754 A1 | 3/2016 | Kostrzewski et al. | |
| 2016/0095710 A1 | 4/2016 | Juszczyk et al. | |
| 2016/0100907 A1 | 4/2016 | Gomes | |
| 2016/0106483 A1 | 4/2016 | Mayer et al. | |
| 2016/0128847 A1 | 5/2016 | Kurtaliaj et al. | |
| 2016/0143744 A1 | 5/2016 | Bojarski et al. | |
| 2016/0157751 A1 | 6/2016 | Mahfouz | |
| 2016/0199101 A1 | 7/2016 | Sharifi-Mehr et al. | |
| 2016/0228192 A1 | 8/2016 | Jansen et al. | |
| 2016/0235447 A1* | 8/2016 | Mundis, Jr. | A61B 17/7031 |
| 2016/0235480 A1 | 8/2016 | Scholl et al. | |
| 2016/0235493 A1 | 8/2016 | LeBoeuf, II et al. | |
| 2016/0242819 A1 | 8/2016 | Simpson | |
| 2016/0242857 A1 | 8/2016 | Scholl | |
| 2016/0242934 A1 | 8/2016 | Van der Walt et al. | |
| 2016/0256279 A1 | 9/2016 | Sanders et al. | |
| 2016/0256285 A1 | 9/2016 | Jansen | |
| 2016/0262800 A1 | 9/2016 | Scholl et al. | |
| 2016/0262895 A1 | 9/2016 | Shea et al. | |
| 2016/0270802 A1 | 9/2016 | Fang et al. | |
| 2016/0270931 A1 | 9/2016 | Trieu | |
| 2016/0274571 A1 | 9/2016 | LaVallee et al. | |
| 2016/0283676 A1 | 9/2016 | Kelly et al. | |
| 2016/0287395 A1 | 10/2016 | Khalili et al. | |
| 2016/0296285 A1 | 10/2016 | Chaoui et al. | |
| 2016/0310221 A1 | 10/2016 | Bar et al. | |
| 2016/0331417 A1 | 11/2016 | Trautwein et al. | |
| 2016/0354009 A1 | 12/2016 | Schroeder | |
| 2016/0354161 A1 | 12/2016 | Deitz | |
| 2016/0360997 A1 | 12/2016 | Yadav et al. | |
| 2017/0000568 A1 | 1/2017 | O'Neil et al. | |
| 2017/0007145 A1 | 1/2017 | Gharib et al. | |
| 2017/0007328 A1 | 1/2017 | Cattin et al. | |
| 2017/0007408 A1 | 1/2017 | Fitz et al. | |
| 2017/0027590 A1 | 2/2017 | Amiot et al. | |
| 2017/0027617 A1 | 2/2017 | Strnad | |
| 2017/0035580 A1 | 2/2017 | Murphy | |
| 2017/0056179 A1 | 3/2017 | Lorio | |
| 2017/0056196 A1 | 3/2017 | Kuiper et al. | |
| 2017/0071503 A1 | 3/2017 | Wasielewski | |
| 2017/0119472 A1 | 5/2017 | Herrmann et al. | |
| 2017/0132389 A1 | 5/2017 | McCauley et al. | |
| 2017/0135706 A1 | 5/2017 | Frey et al. | |

(56) References Cited

U.S. PATENT DOCUMENTS

| | | | |
|---|---|---|---|
| 2017/0135707 A9 | 5/2017 | Frey et al. | |
| 2017/0135770 A1 | 5/2017 | Scholl | |
| 2017/0143426 A1 | 5/2017 | Isaacs et al. | |
| 2017/0143494 A1 | 5/2017 | Mahfouz | |
| 2017/0143502 A1 | 5/2017 | Yadin et al. | |
| 2017/0156798 A1 | 6/2017 | Wasielewski | |
| 2017/0189121 A1 | 7/2017 | Frasier et al. | |
| 2017/0231661 A1* | 8/2017 | Bannigan | A61B 17/7053 606/263 |
| 2017/0231709 A1 | 8/2017 | Gupta et al. | |
| 2017/0252107 A1 | 9/2017 | Turner et al. | |
| 2017/0273718 A1 | 9/2017 | Metzger et al. | |
| 2017/0323037 A1 | 11/2017 | Schroeder | |
| 2017/0360493 A1 | 12/2017 | Zucker et al. | |
| 2018/0078286 A1* | 3/2018 | Le Couedic | A61B 17/7053 |
| 2018/0178148 A1 | 6/2018 | Mazor et al. | |
| 2018/0256067 A1 | 9/2018 | Chen et al. | |
| 2018/0289396 A1 | 10/2018 | McGahan et al. | |
| 2018/0295584 A1 | 10/2018 | Gliner et al. | |
| 2018/0301213 A1 | 10/2018 | Zehavi et al. | |
| 2018/0303552 A1 | 10/2018 | Ryan et al. | |
| 2018/0310993 A1 | 11/2018 | Hobeika et al. | |
| 2018/0349519 A1 | 12/2018 | Schroeder | |
| 2019/0015136 A1 | 1/2019 | Kraemer | |
| 2019/0029733 A1* | 1/2019 | Mickiewicz | A61B 17/7047 |
| 2019/0046269 A1 | 2/2019 | Hedblom | |
| 2019/0046287 A1 | 2/2019 | Fallin et al. | |
| 2019/0059951 A1 | 2/2019 | Barrus | |
| 2019/0060086 A1 | 2/2019 | Krause et al. | |
| 2019/0083144 A1 | 3/2019 | Sharifi-Mehr et al. | |
| 2019/0099221 A1 | 4/2019 | Schmidt et al. | |
| 2019/0103190 A1 | 4/2019 | Schmidt et al. | |
| 2019/0110819 A1 | 4/2019 | Triplett et al. | |
| 2019/0117278 A1 | 4/2019 | Chin | |
| 2019/0122364 A1 | 4/2019 | Zhang et al. | |
| 2019/0142599 A1 | 5/2019 | Thibodeau | |
| 2019/0167314 A1 | 6/2019 | Mosnier | |
| 2019/0201013 A1 | 7/2019 | Siccardi et al. | |
| 2019/0201155 A1 | 7/2019 | Gupta et al. | |
| 2019/0209212 A1 | 7/2019 | Scholl | |
| 2019/0216507 A1* | 7/2019 | Bannigan | A61B 17/7052 |
| 2019/0223916 A1 | 7/2019 | Barrus et al. | |
| 2019/0231443 A1 | 8/2019 | McGinley et al. | |
| 2019/0231557 A1 | 8/2019 | Sutterlin et al. | |
| 2019/0239935 A1 | 8/2019 | Willis et al. | |
| 2019/0247100 A1 | 8/2019 | Mundis et al. | |
| 2019/0254719 A1* | 8/2019 | Gandhi | A61B 17/7011 |
| 2019/0254769 A1 | 8/2019 | Scholl | |
| 2019/0262015 A1 | 8/2019 | Siccardi et al. | |
| 2019/0269463 A1 | 9/2019 | Mosnier | |
| 2019/0343587 A1 | 11/2019 | Mosnier | |
| 2019/0362028 A1 | 11/2019 | Mosnier | |
| 2019/0380782 A1 | 12/2019 | McAfee | |
| 2020/0060768 A1 | 2/2020 | Mosnier | |
| 2020/0121394 A1 | 4/2020 | Mosnier | |
| 2020/0170676 A1* | 6/2020 | Grob | A61B 17/1671 |

FOREIGN PATENT DOCUMENTS

| | | |
|---|---|---|
| AU | 2019200740 A1 | 2/2019 |
| AU | 2019200888 A1 | 2/2019 |
| AU | 2019203557 A1 | 6/2019 |
| CA | 2927955 | 4/2014 |
| CA | 2872845 | 1/2018 |
| CN | 1816134 | 8/2006 |
| CN | 102805677 | 12/2012 |
| CN | 104127229 | 11/2014 |
| CN | 205073000 | 3/2016 |
| CN | 103892953 | 5/2016 |
| CN | 104434287 | 1/2017 |
| CN | 104323843 | 7/2017 |
| CN | 105078555 | 11/2018 |
| EP | 1 570 781 | 7/2005 |
| EP | 2 053 580 | 4/2009 |
| EP | 2 749 235 | 7/2014 |
| EP | 2 754 419 | 7/2014 |
| EP | 2 496 183 | 9/2015 |
| EP | 3 000 443 | 3/2016 |
| EP | 2 608 749 | 8/2016 |
| EP | 2 403 434 | 4/2017 |
| EP | 3 431 032 | 1/2019 |
| FR | 1358988 | 4/1964 |
| FR | 1360208 | 5/1964 |
| JP | 2016-537036 | 12/2016 |
| JP | 2016-540610 | 12/2016 |
| WO | WO 98/55038 | 12/1998 |
| WO | WO 00/53077 | 9/2000 |
| WO | WO 04/017836 | 3/2004 |
| WO | WO 04/089224 | 10/2004 |
| WO | WO 04/111948 | 12/2004 |
| WO | WO 05/074368 | 8/2005 |
| WO | WO 06/075331 | 7/2006 |
| WO | WO 06/084193 | 8/2006 |
| WO | WO 07/035925 | 3/2007 |
| WO | WO 07/038290 | 4/2007 |
| WO | WO 09/124245 | 10/2007 |
| WO | WO 08/002588 | 1/2008 |
| WO | WO 08/079546 | 7/2008 |
| WO | WO 08/124079 | 10/2008 |
| WO | WO 09/119181 | 10/2009 |
| WO | WO 10/044880 | 4/2010 |
| WO | WO 10/064234 | 6/2010 |
| WO | WO 10/121147 | 10/2010 |
| WO | WO 10/147972 | 12/2010 |
| WO | WO 11/021192 | 2/2011 |
| WO | WO 12/012863 | 2/2012 |
| WO | WO 12/113030 | 8/2012 |
| WO | WO 12/131660 | 10/2012 |
| WO | WO 13/003435 | 1/2013 |
| WO | WO 04/030559 | 4/2014 |
| WO | WO 14/191790 | 12/2014 |
| WO | WO 16/102026 | 12/2014 |
| WO | WO 15/040552 | 3/2015 |
| WO | WO 15/054543 | 4/2015 |
| WO | WO 15/056131 | 4/2015 |
| WO | WO 15/079011 | 6/2015 |
| WO | WO 15/089118 | 6/2015 |
| WO | WO 15/185219 | 12/2015 |
| WO | WO 15/195843 | 12/2015 |
| WO | WO 15/200720 | 12/2015 |
| WO | WO 16/019424 | 2/2016 |
| WO | WO 16/019425 | 2/2016 |
| WO | WO 16/019426 | 2/2016 |
| WO | WO 16/26053 | 2/2016 |
| WO | WO 16/032875 | 3/2016 |
| WO | WO 16/044352 | 3/2016 |
| WO | WO 16/048800 | 3/2016 |
| WO | WO 16/012726 | 4/2016 |
| WO | WO 16/088130 | 6/2016 |
| WO | WO 16/094826 | 6/2016 |
| WO | WO 17/001851 | 6/2016 |
| WO | WO 16/137347 | 9/2016 |
| WO | WO 16/148675 | 9/2016 |
| WO | WO 16/165030 | 10/2016 |
| WO | WO 17/039596 | 3/2017 |
| WO | WO 17/064719 | 4/2017 |
| WO | WO 17/066518 | 4/2017 |
| WO | WO 17/077356 | 5/2017 |
| WO | WO 17/079655 | 5/2017 |
| WO | WO 17/127838 | 7/2017 |
| WO | WO 17/151949 | 9/2017 |
| WO | WO 17/221257 | 12/2017 |
| WO | WO 18/045086 | 3/2018 |
| WO | WO 18/055494 | 3/2018 |
| WO | WO 18/055518 | 3/2018 |
| WO | WO 18/078636 | 5/2018 |
| WO | WO 18/087758 | 5/2018 |
| WO | WO 18/131044 | 7/2018 |
| WO | WO 18/131045 | 7/2018 |
| WO | WO 18/183314 | 10/2018 |
| WO | WO 18/185755 | 10/2018 |
| WO | WO 18/193316 | 10/2018 |
| WO | WO 18/193317 | 10/2018 |

(56) References Cited

FOREIGN PATENT DOCUMENTS

| WO | WO 18/203100 | 11/2018 |
|---|---|---|
| WO | WO 18/203101 | 11/2018 |
| WO | WO 19/014452 | 1/2019 |
| WO | WO 19/036039 | 2/2019 |
| WO | WO 19/043426 | 3/2019 |
| WO | WO 19/068085 | 4/2019 |
| WO | WO 19/070729 | 4/2019 |
| WO | WO 19/118844 | 6/2019 |
| WO | WO 19/140240 | 7/2019 |

OTHER PUBLICATIONS

Aurouer et al., 2009, Computerized preoperative planning for correction of sigittal deformity of the spine, Surg. Radiol Anat 31:781-792.

Abe et al. "Scoliosis corrective force estimation from the implanted rod deformation using 3 D FEM analysis", 2015, Scoliosis 10(Suppl 2):52, 6 pages.

Aubin et al. "Preoperative Planning Simulator for Spinal Deformity Surgeries", Spine 2008, 33(20):2143-2152.

Barton et al., Mar./Apr. 2016, Early experience and initial outcomes with patient-specific spine rods for adult spinal deformity, Trending in Orthopedics, 39(2):79-86.

Fiere et al., Jul. 2016, 40. Preoperative planning and patient-specific rods for surgical treatment of thoracolumbar sagittal imbalance, in Surgery of the Spine and Spinal Cord. A Neurosurgical Approach, Van de Kalft ed., Springer International Publishing, Switzerland, pp. 645-662.

Foroozandeh et al., Summer 2012, 3D reconstruction using cubic Bezier spline curves and active contours (case study), Iranian Journal of Medical Physics, 9(3):169-176.

Galbusera et al., Feb. 2019, Artificial intelligence and machine learning in spine research, JOR Spine, 2:E1044, 20 pp.

Grove 2011, Heterogeneous modeling of medical image data using B-spline functions, doctoral dissertation, Department of Computer Science and Engineering, University of South Florida, 212 pp.

Lazarus, Jun. 21, 2013, An introduction to splines, 29 pp.

Li et al., 2009, Modeling and measurement of 3D deformation of scoliotic spine using 2D x-ray images, Lecture Notes in Computer Science, 8 pp.

Lin, Sep. 17-21, 2003, The simplified spine modeling by 3-D Bezier curve based on the orthogonal spinal radiographic images, Proceedings of the 25th Annual International Conference of the IEEE EMBS, Cancun, Mexico, pp. 944-946.

Pasha et al., 2018, Data-driven classification of the 3D spinal curve in adolescent idiopathic scoliosis with an applications in surgical outcome prediction, Scientific Reports, 8:16296, 10 pp.

Poredos et al., 2015, Determination of the human spine curve based on laser triangulation, BMC Medical Imaging 15(2):1-11.

Prautzsch et al., Mar. 26, 2001, Bezier-and B-spline techniques, 58 pp.

Ratnakar et al. 2011, Predicting thoracic spinal postures in finite element model with Bezier technique, Ircobe Conference 2011, IRC-11-57, 4 pp.

Reinshagen et al. "A novel minimally invasive technique for lumbar decompression, realignment, and navigated interbody fusion", J Clin Neurosci. 2015, 22(9):1484-1490; XP055503028.

Rickert et Al., "Posterior lumbar interbody fusion implants", Orthopaede, Springer Verlag, Berlin, DE vol. 44, No. 2 dated Jan. 28, 2015 pp. 162-169.

Solla et al., Mar. 2019, Patient-specific rods for surgical correction of sagittal imbalance in adults: Technical aspects and preliminary results, Clin Spine Surg, 32(2), 7 pp.

Spontech Medical AG Vertaplan—die Software für Wirbelsäulenchirurgen, Aug. 29, 2013 Retrieved from the Internet: URL: https://www.youtube.com/watch?v=q0qhW1T1cp8 in 1 page.

International Search Report and Written Opinion in PCT Application PCT/IB2014/065150, dated Oct. 8, 2014 in 9 pages.

International Search Report in PCT Application PCT/IB2014/064586, dated Dec. 23, 2014, in 2 pages.

International Search Report in PCT Application PCT/US2016/060676, dated Nov. 5, 2017 in 7 pages.

International Search Report and Written Opinion in PCT Application PCT/IB2018/000551, dated Dec. 12, 2018 in 9 pages.

International Search Report and Written Opinon in PCT Application PCT/IB2018/000557 dated Oct. 24, 2018 in 12 pages.

* cited by examiner

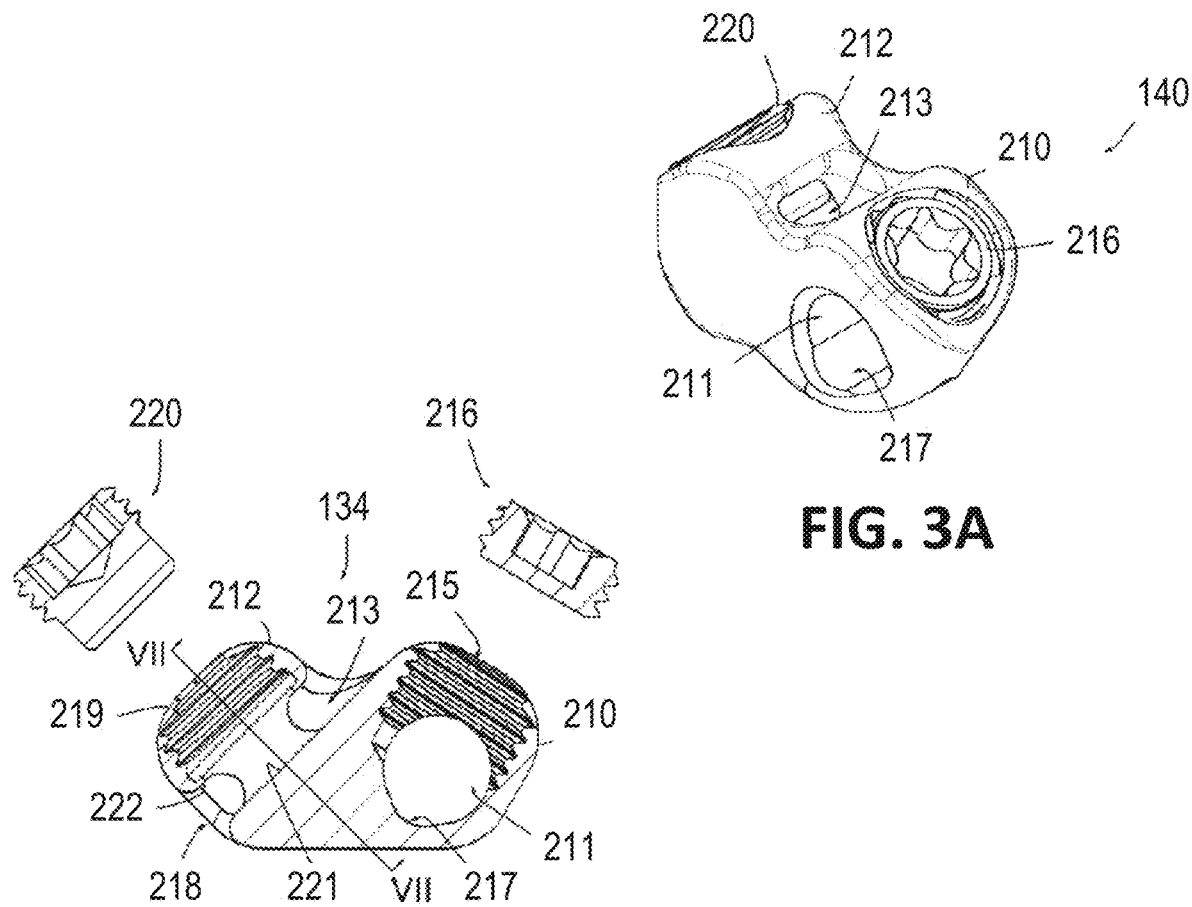
FIG. 3A
FIG. 3B
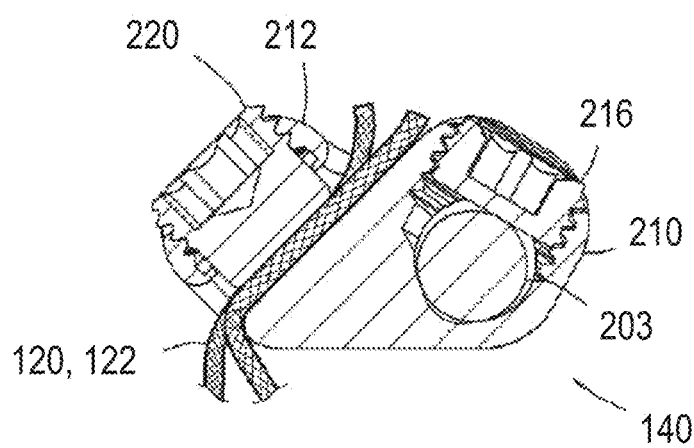
FIG. 3C

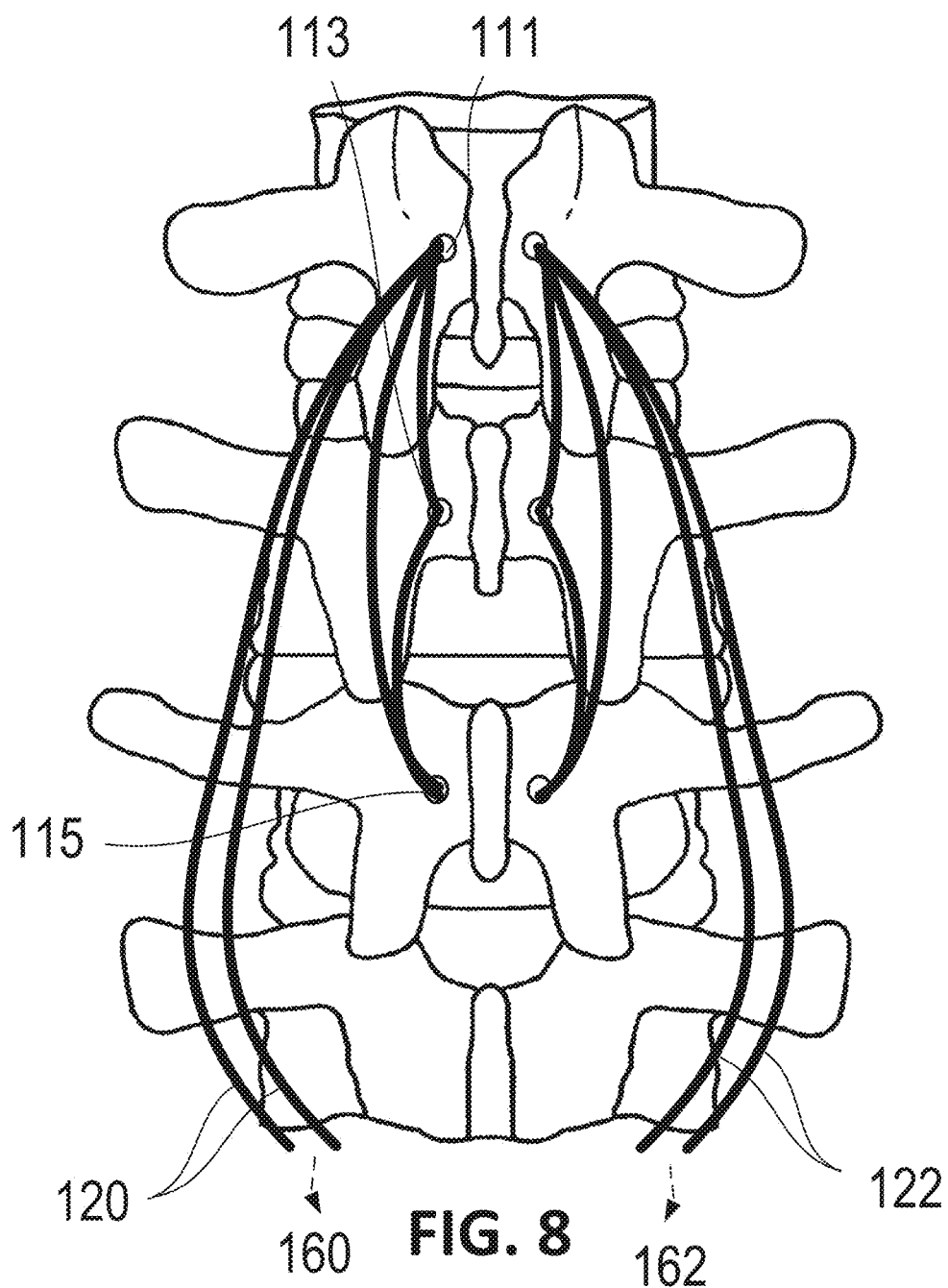

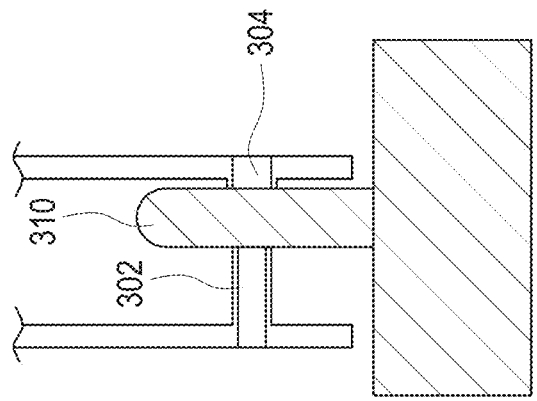
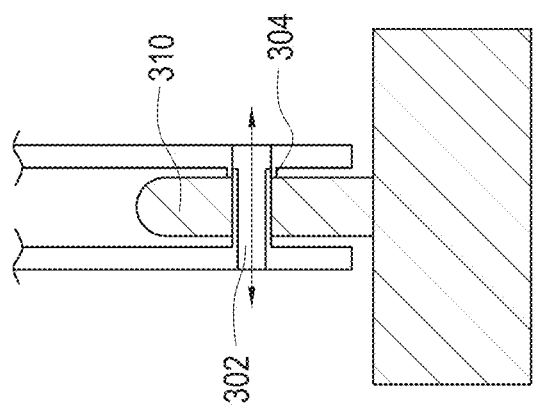
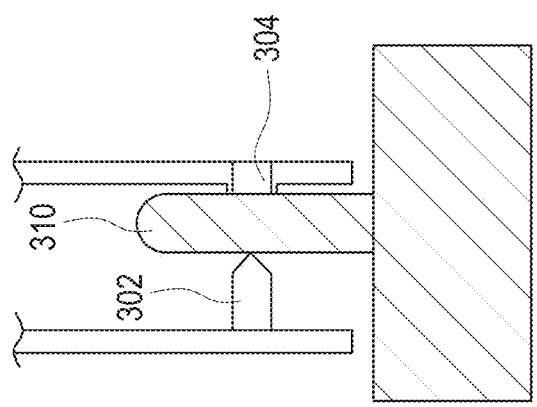
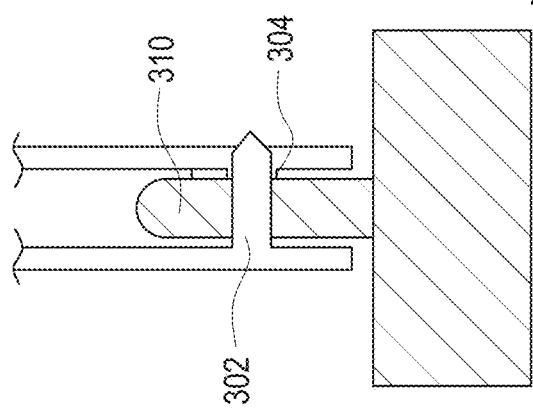
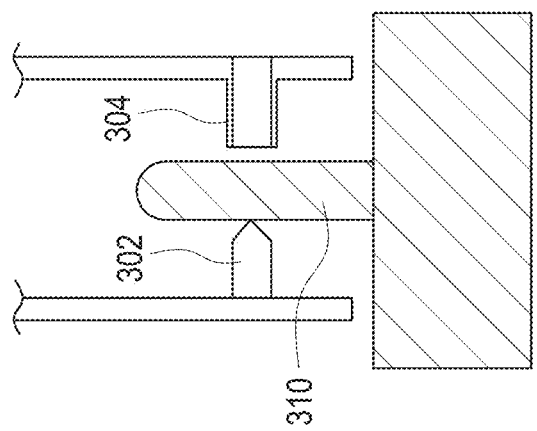
FIG. 11
FIG. 12
FIG. 13

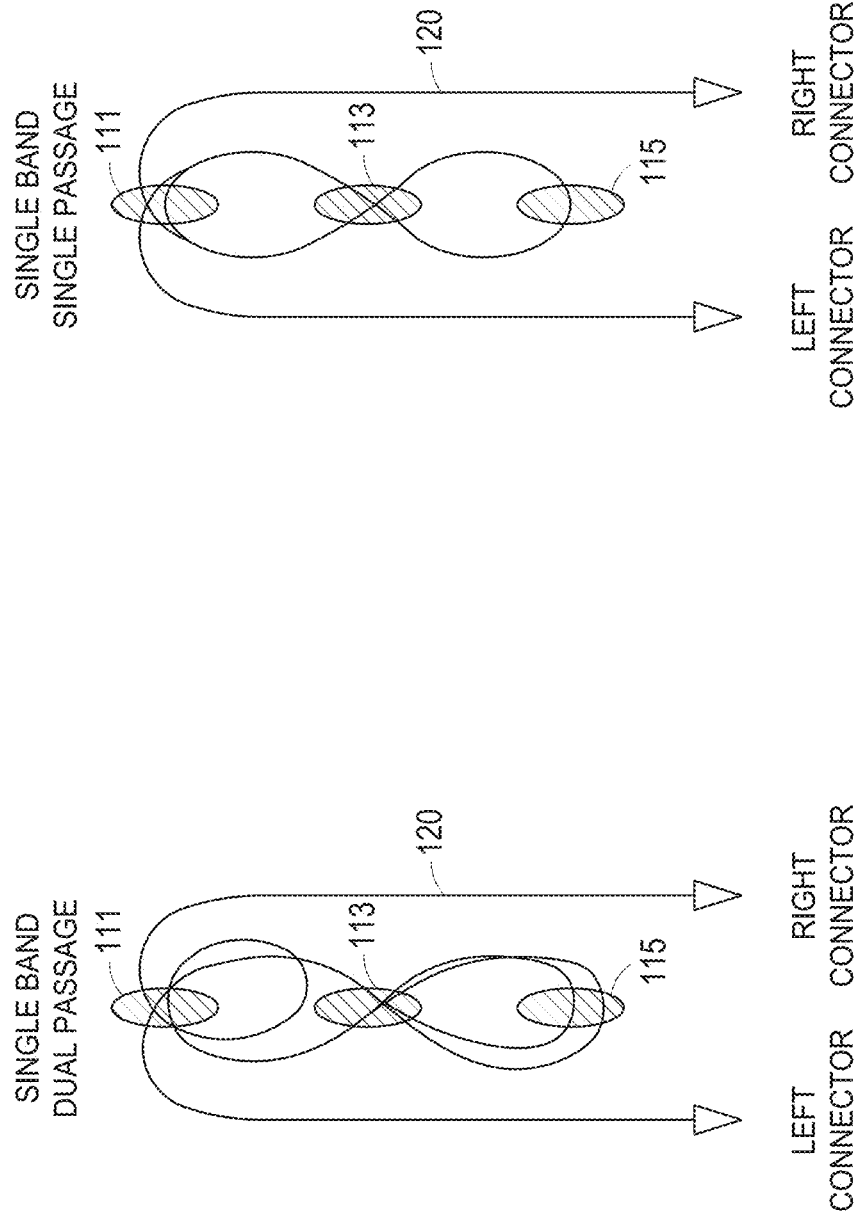

US 10,918,422 B2

METHOD AND APPARATUS FOR INHIBITING PROXIMAL JUNCTIONAL FAILURE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to vertebral stabilization, and, more specifically, devices and methods to inhibit adjacent level kyphosis and/or adjacent level failure such as proximal junctional failure.

Description of the Related Art

Adjacent level failure is a failure of a vertebral column that may follow a less serious condition of adjacent level kyphosis, which is an increased posterior convexity of the vertebral column as viewed from the side. Adjacent level kyphosis and failure, particularly proximal junction kyphosis (PJK) and proximal junction failure (PKF), are known complications for patients who undergo spinal surgery (e.g., spinal fusion surgery). To straighten a distracted spine (e.g., scoliosis), it is known to use vertebral osteosynthesis equipment including, but not limited to, anchoring members for anchoring to the vertebrae (e.g., pedicle screws and/or lamina hooks), connecting rods, and connectors for connecting the rods to the anchoring members, to form a rigid posterior instrumentation construct. However, a spine of the patient who underwent spinal surgery using conventional posterior instrumentation may experience increased loading on vertebral segments adjacent to the instrumentation. The increased load in the adjacent segments may result in adjacent level kyphosis and/or even failure, which may require a repeat, revisionary surgery.

The prevalence and consequences of PJK and PJF are not fully understood. However, different authors have reported the prevalence of PJK following spinal deformity fusion surgeries as ranging from 20% to 39%. The prevalence of PJF has been reported to range between 1.4% and 35%. The cost of revision surgery following PJF has been estimated to be about $77,000.

SUMMARY

The systems, methods, and devices of this disclosure each have several innovative aspects, no single one of which is solely responsible for the desirable attributes disclosed herein.

The present disclosure provides instruments and methods for inhibiting adjacent junctional failure such as proximal junctional failure in a patient having posterior spinal instrumentation. An embodiment of the method can comprise the steps of creating a first transverse bore through a spinous process of a vertebral body of a spine, superior and adjacent an uppermost instrumented vertebral body. A second transverse bore is created through a spinous process of the uppermost instrumented vertebral body. An optional third transverse bore may be created through a spinous process of a vertebral body inferior and adjacent the uppermost instrumented vertebral body;

A tensioning band is threaded through the first, second and third bores, and proximally retracted to bias the upper and lower spinous processes together and also to bias all involved spinous processes in an inferior direction. The tension band is locked with respect to the spine to maintain tension.

The locking step may comprises attaching a connector to the posterior instrumentation and locking the tension band to the connector. Alternatively the locking step comprises attaching a connector to the spine and locking the tension band to the connector.

The tension band may have first and second ends, and both the first and second ends exit the first transverse bore and are locked under tension to a connector secured with respect to the spine. The spinal instrumentation may include a left rod and a right rod, and the tension band is secured to the connector at a point that is medial to the left and right rods.

The creating a first transverse bore step may comprise locating opposing jaws of a bone punch on opposing sides of the spinous process, and punching the first transverse bore. The method may additionally comprise the step of inserting a liner into at least the first transverse bore, prior to the threading a tension band step. The inserting a liner step may comprise inserting a grommet into at least the first transverse bore.

The stabilization or force distribution system of the present invention seeks to modify the forces across the UIV and UIV-1 junction, possibly supplementing the interspinous and supraspinous ligament complexes above the upper instrumented level. In one implementation of the invention, the spinous process of the uppermost and the lowermost of the selected group of three vertebral bodies centered on UIV will be biased towards each other, and all three will be biased in an inferior direction and held in place by locking such as to the posterior instrumentation.

Also disclosed herein are embodiments of a method of inhibiting proximal junctional failure in a patient having posterior spinal instrumentation, comprising the steps of creating a first transverse bore through a spinous process of a vertebral body of a spine, superior and adjacent an uppermost instrumented vertebral body, a second transverse bore through a spinous process of the uppermost instrumented vertebral body, and a third transverse bore through a spinous process of a vertebral body inferior and adjacent the uppermost instrumented vertebral body, threading a tension band having a first end and a second end through the first, second and third bores, extending the tension band inferiorly of the third transverse bore, under tension, and locking the tension band with respect to the spine.

In some embodiments, the locking can comprise attaching a connector to the posterior spinal instrumentation and locking the tension band to the connector. In some embodiments, the locking can comprise attaching a connector to the spine and locking the tension band to the connector. In some embodiments, the tension band has first and second ends, and both the first and second ends exit the first transverse bore and are locked under tension to a connector secured with respect to the spine. In some embodiments, the posterior spinal instrumentation can include a left rod and a right rod, and the tension band is secured to the connector at a point that is medial to the left and right rods.

In some embodiments, the creating a first transverse bore step can comprise locating opposing jaws of a bone punch on opposing sides of the spinous process, and punching the first transverse bore. In some embodiments, the method can further comprise inserting a liner into at least the first transverse bore, prior to the threading a tension band step. In some embodiments, the inserting the liner can comprise inserting a grommet into at least the first transverse bore.

In some embodiments, the tension band can extend through the first bore in a first direction, the second bore in a second direction generally opposite the first direction, and the third bore in the first direction, wherein the first end of the tension band is located one a first side of the spinous process and where the second end of the tension band is located on a second side of the spinous process. In some embodiments, the second end of the tension band can extend through the first bore in the first direction. In some embodiments, the method can further comprise extending a second tension band having a first end and a second end through the first bore, the second bore, and the third bore. In some embodiments, the second tension band can extend through the first bore in the second direction, the second bore in the first direction, and the third bore in the second direction, wherein the first end of the second tension band is located on the second side of the spinous process and the first end of the second tension band is located on the first side of the spinous process. In some embodiments, the second end of the second tension bands can extend through the first bore in the second direction.

Also disclosed herein are embodiments of a system of inhibiting proximal junctional failure in a patient having posterior spinal instrumentation, the system comprising at least one tension band having a first end and a second end, at least one connector configured to be attached to the patient's spine or the posterior spinal instrumentation, wherein the at least one tension band is configured to pass through a plurality of transverse bores in at least two vertebrae of the patient's spine, wherein the first end of the at least one tension band and the second end of the at least one tension band are locked under tension in the at least one connector.

In some embodiments, the system can further comprise a bone punch configured to create the plurality of transverse bores. In some embodiments, the system can comprise a plurality of connectors and wherein the first end of the at least one tension band is locked under tension in a first of the plurality of connectors and the second end of the at least one tension band is locked under tension in a second of the plurality of connectors. In some embodiments, the first of the plurality of connectors and the second of the plurality of connectors can be configured to be located on opposite transverse sides of the patient's spine. In some embodiments, the at least one tension band can comprise a first tension band and a second tension band each having a first end and a second end, and wherein the at least one connector comprises a first connector and a second connector, wherein the first end and the second end of the first tension band are locked under tension in the first connector, and wherein the first end and the second end of the second tension band are locked under tension in the second connector.

In some embodiments, the first connector and the second connector can be configured to be located on opposite transverse sides of the patient's spine.

Further disclosed herein are embodiments of a kit which can include the system/equipment discussed herein.

Any feature, structure, or step disclosed herein can be replaced with or combined with any other feature, structure, or step disclosed herein, or omitted, depending upon the desired clinical result. For purposes of summarizing the disclosure, certain aspects, advantages and novel features of the embodiments have been described herein. It is to be understood that not necessarily any or all such advantages may be achieved in accordance with any particular embodiment of the invention disclosed herein. Thus, the invention may be embodied or carried out in a manner that achieves or optimizes one advantage or group of advantages as taught or suggested herein without necessarily achieving other advantages as may be taught or suggested herein. No individual aspects of this disclosure are essential or indispensable.

All of these embodiments are intended to be within the scope of the present disclosure. Further features and advantages of the embodiments will become apparent to those skilled in the art in view of the Detailed Description which follows when considered together with the attached drawings and claims, the invention not being limited to any particular preferred embodiment(s) disclosed.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIG. 3A illustrates a perspective view of an embodiment of a connector described herein.

FIG. 3B illustrates a cross-section view of the connector of FIG. 3A in a longitudinal direction, two tightening screws of the connector being out of their tapped receiving bores.

FIG. 3C illustrates a cross-section view of the connector of FIG. 3A in a longitudinal direction, when the connector is engaged on a connecting rod, a ligament is engaged thereon, and the tightening screws are placed in the receiving bores.

FIGS. 7-8 illustrate a posterior view of a vertebral column illustrating an embodiment of a method or system explained herein.

FIGS. 9-13 illustrate example distal ends of an embodiment of a pliers type instrument as discussed herein.

FIGS. 20A-20B illustrate an embodiment of a method of installing a single tension band into a vertebral column.

DETAILED DESCRIPTION

Disclosed herein are embodiments of systems, methods, assemblies, and devices which can be incorporated into spinal deformity surgery. Advantageously, tension can be applied onto a patient's spine which can prevent the need for further corrective surgery (e.g., revision surgery). The disclosed techniques and equipment can be used with previously installed spinal equipment, as well as during new surgical procedures. Further, modifications can be made to previously installed spinal equipment in order to incorporate the below disclosed techniques. Advantageously, the disclosed systems can keep the integrity of the supra and intra spinous ligament and focus on anchorage through the spinous process.

Spinal deformity surgery commonly involves implantation of multilevel spinal fusion instrumentation to reshape and rigidly constrain a section of the spine. Post-surgery, a patient may experience an increase in spinal stiffness and an increased loading within spinal segments adjacent to the end of the instrumentation. The increased load in the adjacent segments may result in adjacent level kyphosis or failure, which may require revision surgery. Thus, vertebral osteosynthesis equipment which is configured to distribute the increased loading within adjacent segments to other segments would be desirable to minimize the occurrence of or reduce the severity of adjacent level kyphosis and/or failure.

Figure 1A:
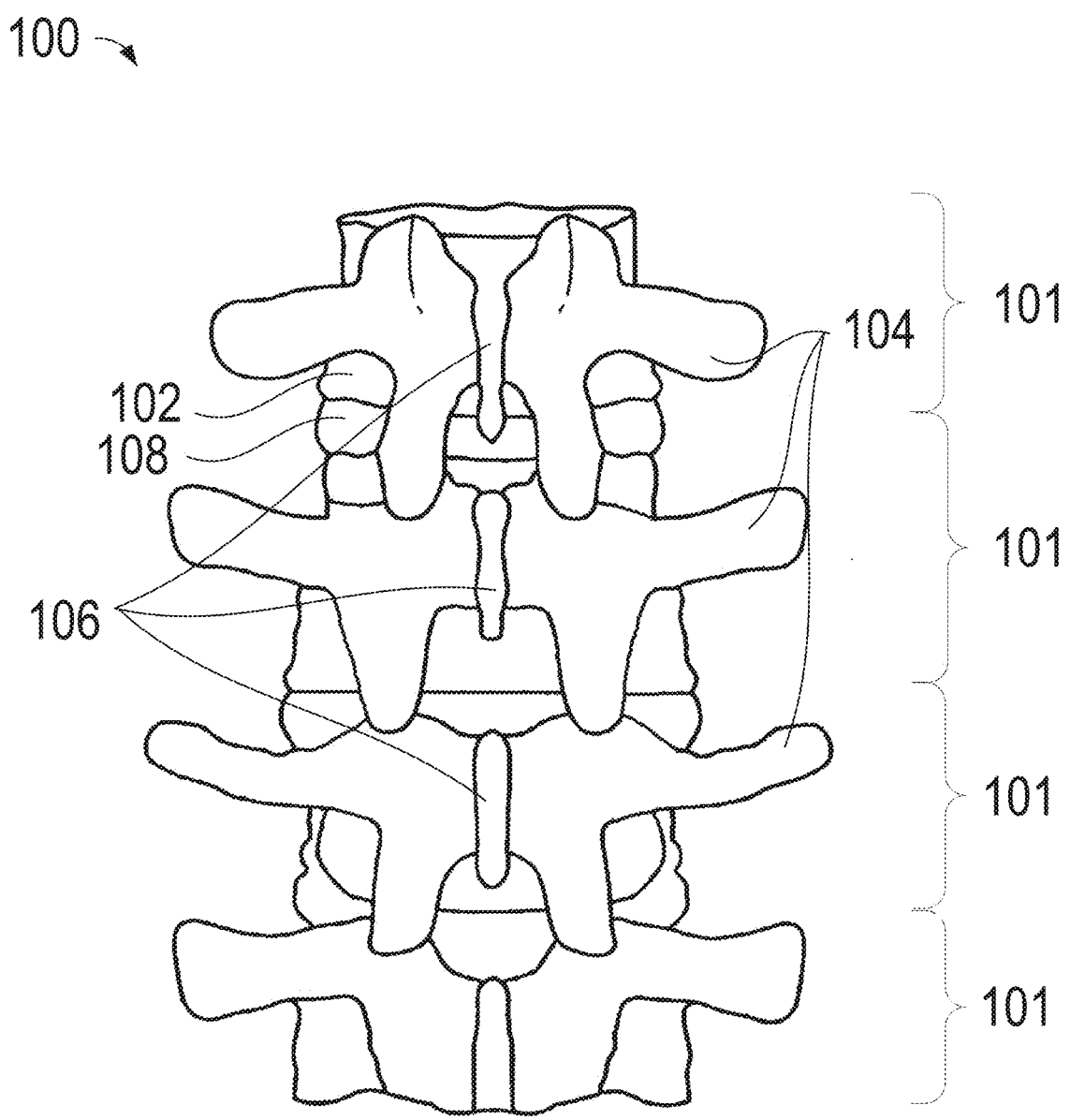
FIG. 1A illustrates a posterior view of a vertebral column.
Figure 1B:
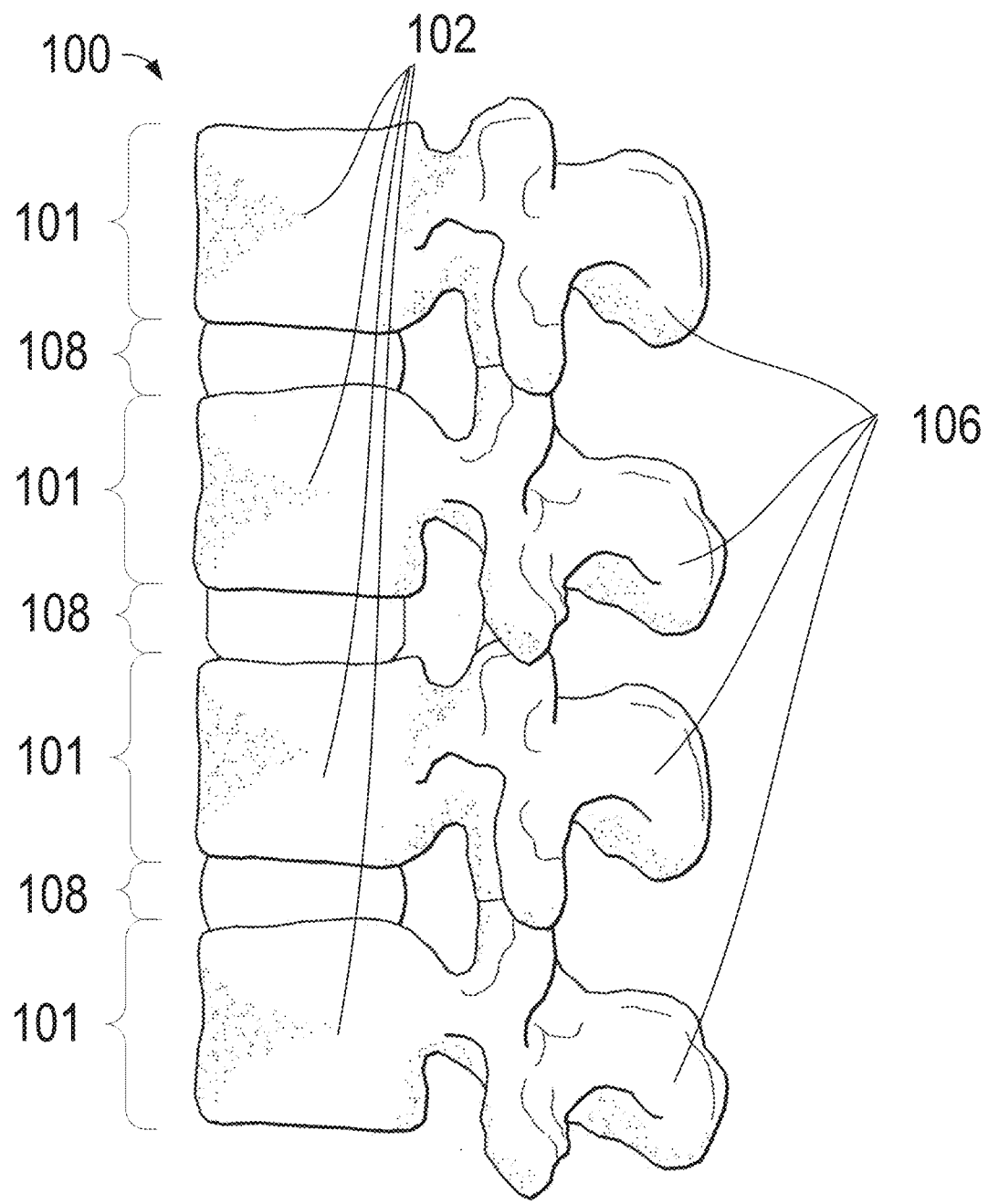
FIG. 1B illustrates a sagittal view of the vertebral column of FIG. 1A.

FIGS. 1A and 1B illustrate posterior and sagittal views of a vertebral column 100, respectively. The vertebral column 100 comprises a series of vertebrae 101. Each vertebra 101 comprises a vertebral body 102, two transverse processes 104 whose ends at least partially point to lateral directions (e.g., left and right directions, respectively), and a spinous process 106 whose end dominantly points to the posterior direction. Each set of adjacent vertebral bodies are separated by an intervertebral disc 108.

Figure 2A:
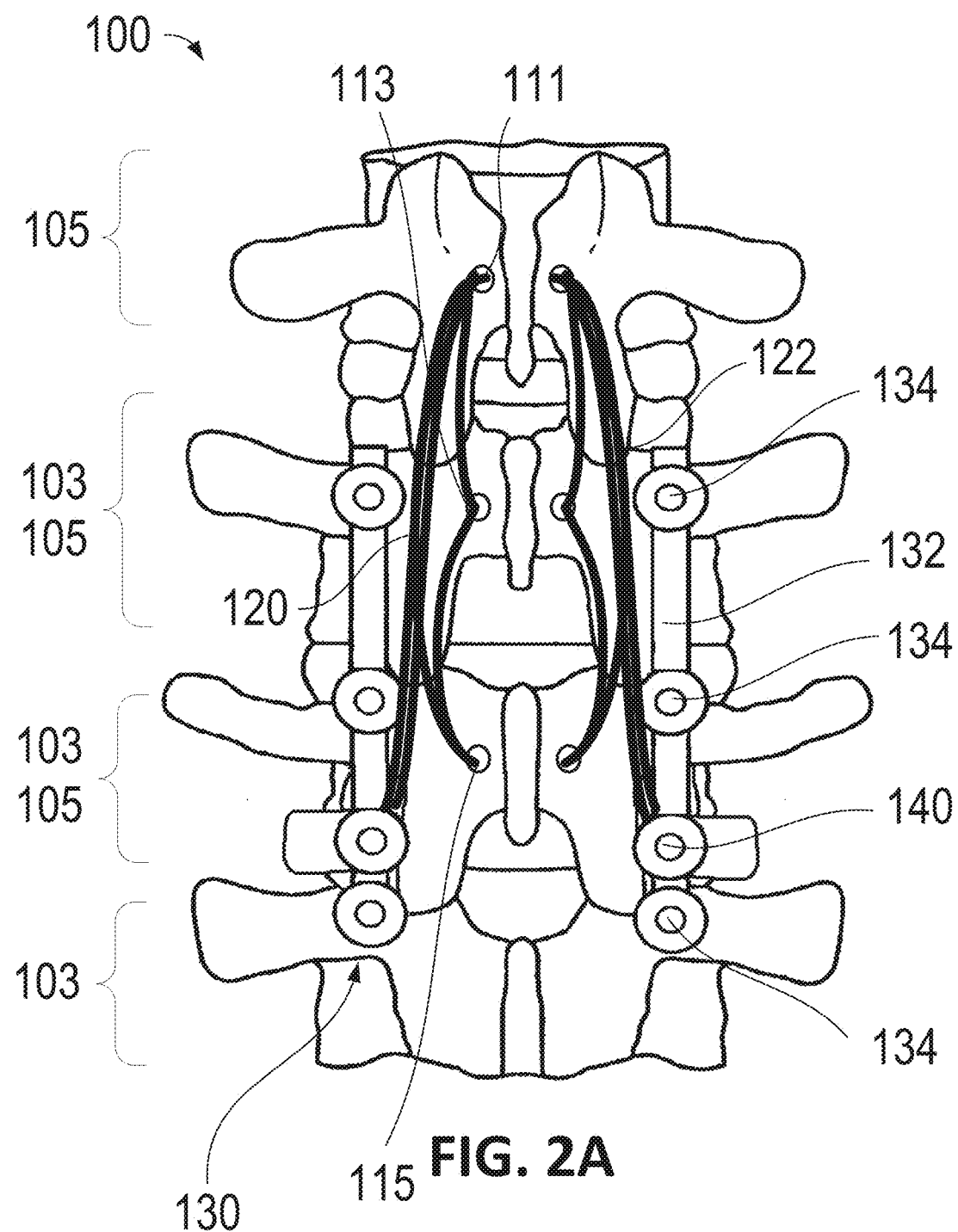
FIG. 2A illustrates a posterior view of a vertebral column with an embodiment of vertebral osteosynthesis equipment described herein.
Figure 2B:
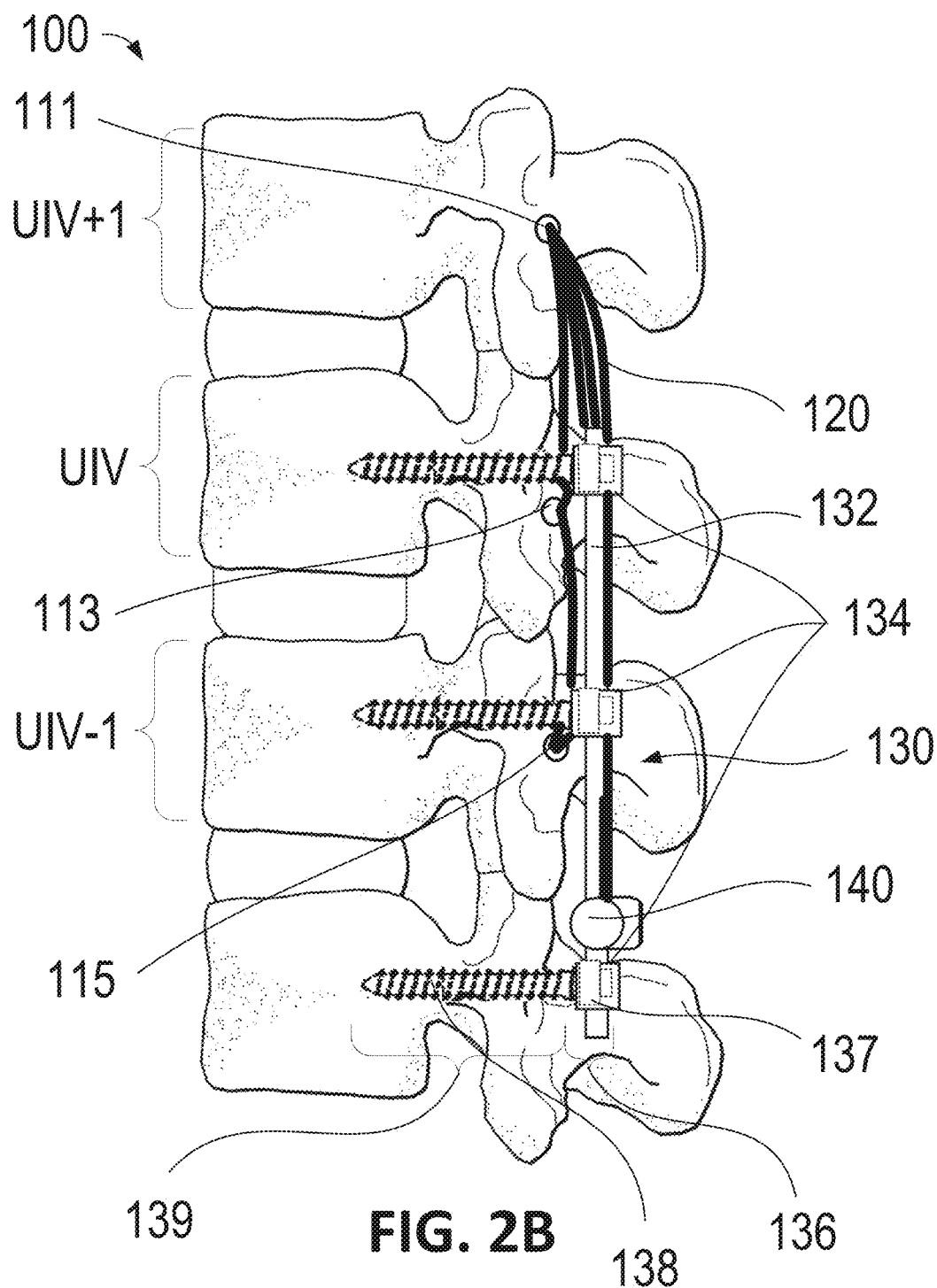
FIG. 2B illustrates a sagittal view of the vertebral column of FIG. 2A.

FIGS. 2A and 2B illustrate posterior and sagittal views of the vertebral column 100 with conventional vertebral osteosynthesis equipment 130 as well as a junction stabilization system in accordance with certain implementations of the present disclosure. With reference to FIGS. 2A-2B, the vertebral osteosynthesis equipment 130 includes one or more rods 132 and one or more screws 134 (e.g., pedicle screws and/or lamina hooks) and may further include one or more transverse connecting rods as is understood in the art. The rods 132, screws 134 and connecting rods thus rigidly hold the vertebrae 101 in place. Each of the one or more connecting rods 132 may be mounted on the left or right side of the vertebral column 100 along the longitudinal length of the vertebral column 100. The one or more connecting rods 132 may extend along the longitudinal lengths of two or three or more vertebrae 101. In one example, as shown in FIG. 2A, the vertebral osteosynthesis equipment 130 may comprise two connecting rods 132, and the two connecting rods 132 may be mounted one on the left and one on the right side of the spinous process 106 near the bases of the transverse processes 104 of the vertebrae 101. The two connecting rods may span along the longitudinal lengths of three or four or more adjacent vertebrae 103. In some embodiments, the one or more connecting rods 132 may be cylindrically shaped and may be made of metal such as stainless steel, titanium, or nitinol. In some embodiments, the equipment 130 may not need to be modified for attachment of the disclosed systems. In alternate embodiments, modifications may be made.

With reference to FIG. 2B, the one or more screws 134 (e.g., pedicle screws and/or lamina hooks) are configured to anchor the one or more connecting rods 132 to or near the bases of the transverse processes 102 of the vertebrae 101 (e.g., laminae). That way, the one or more screws 134 are configured to hold the one or more vertebrae 101 together. Each screw 134 comprises a head 136 and an anchor 138 such as a threaded shaft. The head 136 includes a bore 137 through which one of the one or more connecting rods 132 is configured to pass and a fastener 138 configured to fasten the head 136 of the screw 134 to the connecting rod 132. In one example, as shown in FIG. 2B, the fastener 138 may comprise a screw with threads that are configured to be placed into a transverse hole whose length is perpendicular to that of the bore 137 and interlock with threads on the inner surface of the transverse hole. The anchor 138 is configured to be inserted (e.g., drilled, etc.) into the base of the transverse process 102 of the vertebra 101 and hold the screw 134 inside the vertebra 101. In one example, as shown in FIG. 2B, the anchor 138 may comprise an elongate body with threads on its surface. When the anchor 138 is inserted by rotation into the vertebra 101, the threads of the anchor 138 are configured to facilitate anchoring of the screw 134 to the vertebra 101. While a particular approach is disclosed with respect to FIGS. 2A-2B, the below disclosed techniques can be utilized with variations of equipment and attachment techniques.

FIG. 2B identifies the uppermost instrumented vertebra (UIV) as well as the UIV−1 and UIV+1 adjacent vertebral bodies. The stabilization or force distribution system of the present disclosure seeks to modify the forces across the UIV and UIV−1 junction, possibly supplementing the interspinous and supraspinous ligament complexes above the upper instrumented level. Alternatively, the system may be used on the lowermost instrumented vertebra (LIV) or any vertebra in between. This may be accomplished using the tension/band/strap system described in greater detail below, to secure the UIV−1 through UIV+1 spinous processes together. Alternatively, the stabilization system may be used to secure UIV or UIV−1 to UIV+1 or UIV+2 or higher, including all intervening spinous processes, depending upon the desired clinical response. The secured group of spinous processes can then be biased downwardly by the stabilization system (such as a band and connector as discussed below), which can be thereafter locked with respect to the spine. The band may be locked to a spine screw, a rod, a transverse bar or directly to the spine such as by wrapping around bony structures or passing through a bore created for that purpose, and the particular connection is not limiting.

Thus, in accordance with one aspect of the present disclosure, a selected group of two or three or more adjacent vertebral bodies can be secured together in a manner that distributes forces experienced at the junction between an instrumented vertebral body and an adjacent uninstrumented vertebral body. For example, if the superior most instrumented vertebral body UIV is T10, the three vertebral bodies T9-T11 will preferably be stabilized as described herein. However, more or less vertebral bodies can be stabilized as well. For example T9-T10, T10-T11, T8-T12, T8-T11, or T9-T12. In some embodiments, two, three, four, five, six, seven, eight, nine, or ten vertebral bodies can be stabilized together. In some embodiments, more than two, three, four, five, six, seven, eight, nine, or ten vertebral bodies can be stabilized together. In some embodiments, less than three, four, five, six, seven, eight, nine, or ten vertebral bodies can be stabilized together. In one implementation, the spinous process of the uppermost and the lowermost of the selected group of three vertebral bodies centered on UIV (or LIV) will be biased towards each other, and all three will be biased in an inferior direction and held in place by locking to the posterior instrumentation. This may be accomplished using any of a variety of customized clamps or fixtures, or, as described in greater detail below, by weaving one or two or more flexible tension bands through and or around the spinous process of the involved vertebral bodies.

With reference to FIG. 2A, at least a first tension band 120 and preferably also a second tension band 122 are configured to pass through holes (e.g., punches, lumens) 111, 113 and 115 through the spinous process on the vertebrae 101 and bias the spinous processes together. The holes can extend through other portions of the vertebrae as well. The tension band (e.g., strap, cord, wires) may be, for example, Mersilene tape (Ethicon, Summerville, N.Y.) or other flexible implant grade material having sufficient resistance to elongation. The tension bands may alternatively be made of woven or multi-strand metallic materials such as Nitinol or stainless steel, or polymeric materials such as polyester, polyamide, polyethylene, polyethylene polycarbonate, poly (ethylene terephthalate) (PET), and polyetheretherketone (PEEK). In other embodiments, the one or more tension band 120 and/or 122 may be made of plaits of polyester fibers, with a circular or flat section. In some embodiments, the tension band 120/122 may be the same, and in alternate embodiments they may differ in, for example, size, shape, or material. The particular material/dimensions of the tension band wires 120/122 are not limiting.

In one example, as shown in FIG. 2A, the tension bands 120 and 122 may be configured to pass through holes 111, 113 and 115 on three adjacent vertebrae 105, two of which are secured by bone screws to connecting rods 132, such that the woven tension band construct spans the proximal junction. The two ends of each of the tension bands 120 and/or 122 may be anchored to the one or more connectors 140, or directly to existing equipment or lower vertebrae. In some embodiments, the tension band 120/122 may not pass through holes, but instead may be attached directly to the vertebrae 105, such as at a radially outermost surface. In some embodiments, the tension band 120/122 may pass through empty spaces in or between vertebrae.

With reference to FIG. 2B, the connectors 140 are configured to anchor free ends of each of the tension bands 120 and 122, or other portions of the tension band 120 and 122. The connectors 140 can have a locking interface such as a bore (not illustrated) for receiving a connecting rod 132 or a transverse bar (not illustrated). The connector 140 as illustrated is coupled to a corresponding connecting rod 132, such as with the connecting rod 132 clamped inside the bore of the connector 140. In one example, as shown in FIG. 2B, a left and a right connector 140, are each coupled to a corresponding left and right connecting rods, respectively, via the locking interfaces (not shown) of the connectors 140.

In the construct illustrated in FIG. 2A, both free ends of the first band 120 extend inferiorly on the left side of the spine, and both free ends of the band 122 extend inferiorly on the right side of the spine. Each of the first and second bands 120/122 may be provided with unique first and second connectors. Alternatively, the free ends of both the first and second bands 120/122 may be locked to a single connector. In a single connector embodiment, the connector is preferably located along the sagittal plane to provide a slightly medially directed bias on the bands, though the particular position is not limiting. The single connector may be carried by a transverse bar, or may include a first locking interface for connecting to a first rod and a second locking interface for connecting to a second rod. In a two connector implementation, the first and second connectors may be located such that the longitudinal axis of the segments of the bands between the aperture 111 and the point of attachment to the connector extend downwardly approximately parallel to the sagittal plane or inclined medially in the downward direction, though again the particular positioning is not limiting.

FIGS. 3A-3C illustrates the detailed structure of one connector 140 useful for connecting the tension band to the instrumentation. The connector 140 is configured to secure the one or both ends of a tension band to the posterior instrumentation, such as to connecting rod 132. With reference to FIG. 3A, the connector 140 includes a first portion 210, in which a first locking interface such as conduit 211 is formed for engaging on the connecting rod 132, and a second portion 212 in which a second conduit 213, for receiving the one or more tension bands 120 and/or 122, is formed side-by-side.

With reference to FIGS. 3B-3C, the first conduit 211 communicates with a tapped bore 215 for receiving a screw/bolt/attachment member 216 for tightening the connecting rod 132 in said conduit 211. This conduit 211 can include, on the side diametrically opposite the bore 215, a rounded longitudinal recess 217 whereof the connection to the rest of the conduit 211 forms two longitudinal edges (shown in FIG. 3B). The presence of these edges is favorable to complete immobilization of the connector 140 in rotation relative to the bar 130 when the screw 216 is tightened. In alternative embodiments, the edges may not be included. In further alternate embodiments, more significant edges (e.g., triangular, rectangular, polygonal shaped) may be incorporated to further immobilize.

The second conduit 213 is separate from the first conduit 211 and is not in communication therewith. In alternate embodiments, they may be connected. It can be rectilinear between the opening 218 for insertion therein of the one or two or more tension band wires 120 and/or 122 and the opening 213 opposite that conduit 211. The latter may be formed at an angle such as about 45° relative to a length of the connector 140 defined jointly by said first portion 210 and second portion 212, such that the opening 218 emerges on a side of the second portion 212 substantially opposite the first portion 210, or remote from said first portion 210. In some embodiments, where a single connector 140 is used, the connector 140 can contain an additional conduit so that each tension band 120/122 is in a separate conduit. U.S. Pat. No. 9,314,275, issued Apr. 19, 2016, describes the connector in greater detail and is hereby incorporated by reference in its entirety herein.

Each of the connecting rod conduit 211 and tension band conduit 213 has a central longitudinal axis which extends approximately in parallel with the side walls of the respective conduit. The longitudinal axis of the second conduit 213 may be oriented relative to the longitudinal axis of the first conduit 211 such that when the connector is mounted to a posterior rod, the longitudinal axis of the second conduit 213 extends at an angle of no more than about 25°, preferably no more than about 15°, and more preferably within about 5° of the straight line between the closest opening of second conduit 213 and the spinous process bore from which the tension band exits, typically the first transverse bore. The point at which the tension band enters the connector is typically at a point that is medial to the left and right posterior fusion rods, and preferably within about 1.0 inches or 0.75 inches or 0.5 inches of the sagittal plane of the spine.

Figure 4A:
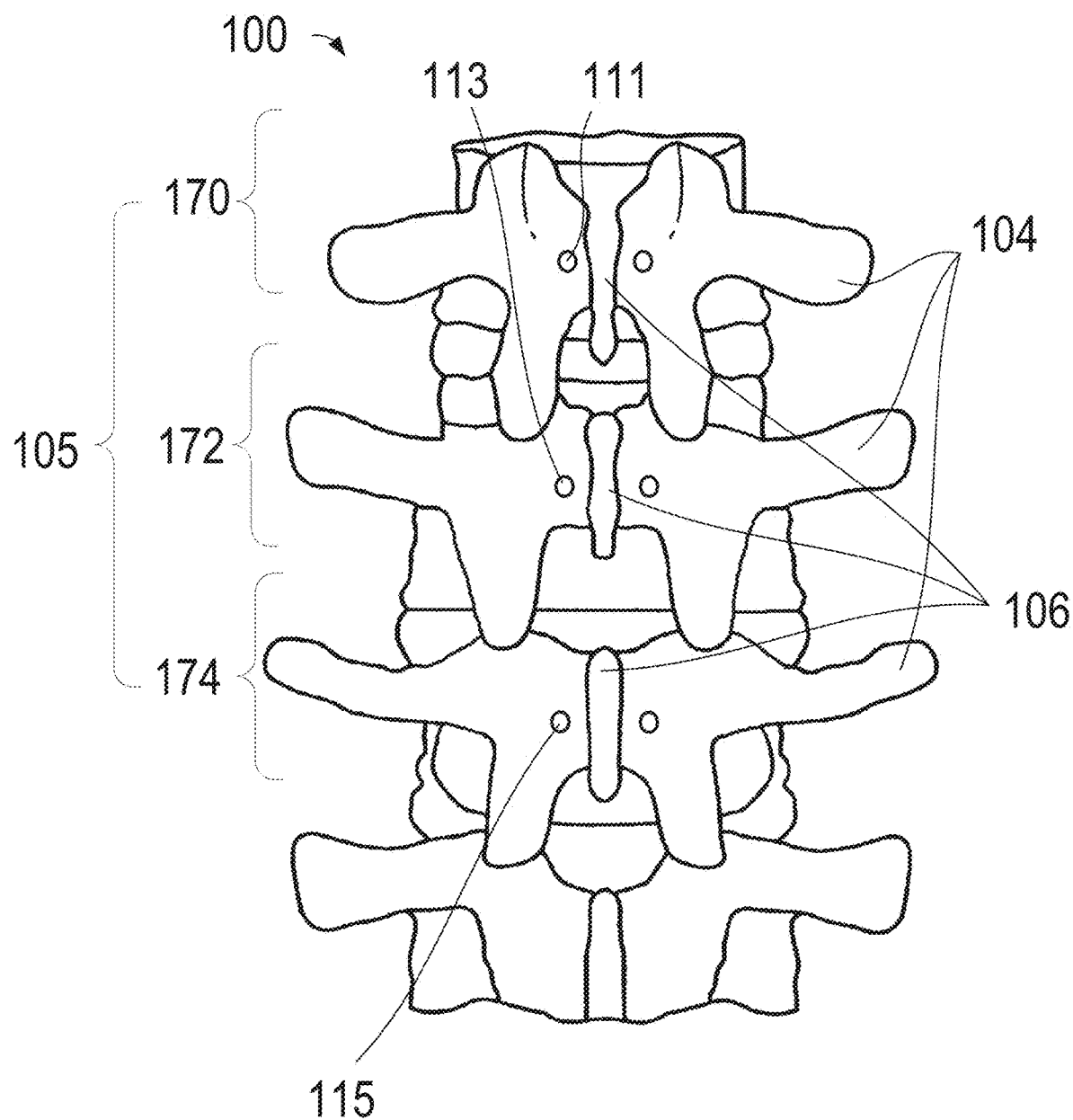
FIG. 4A illustrates a posterior view of the vertebral column illustrating an embodiment of a method explained herein.
Figure 4B:
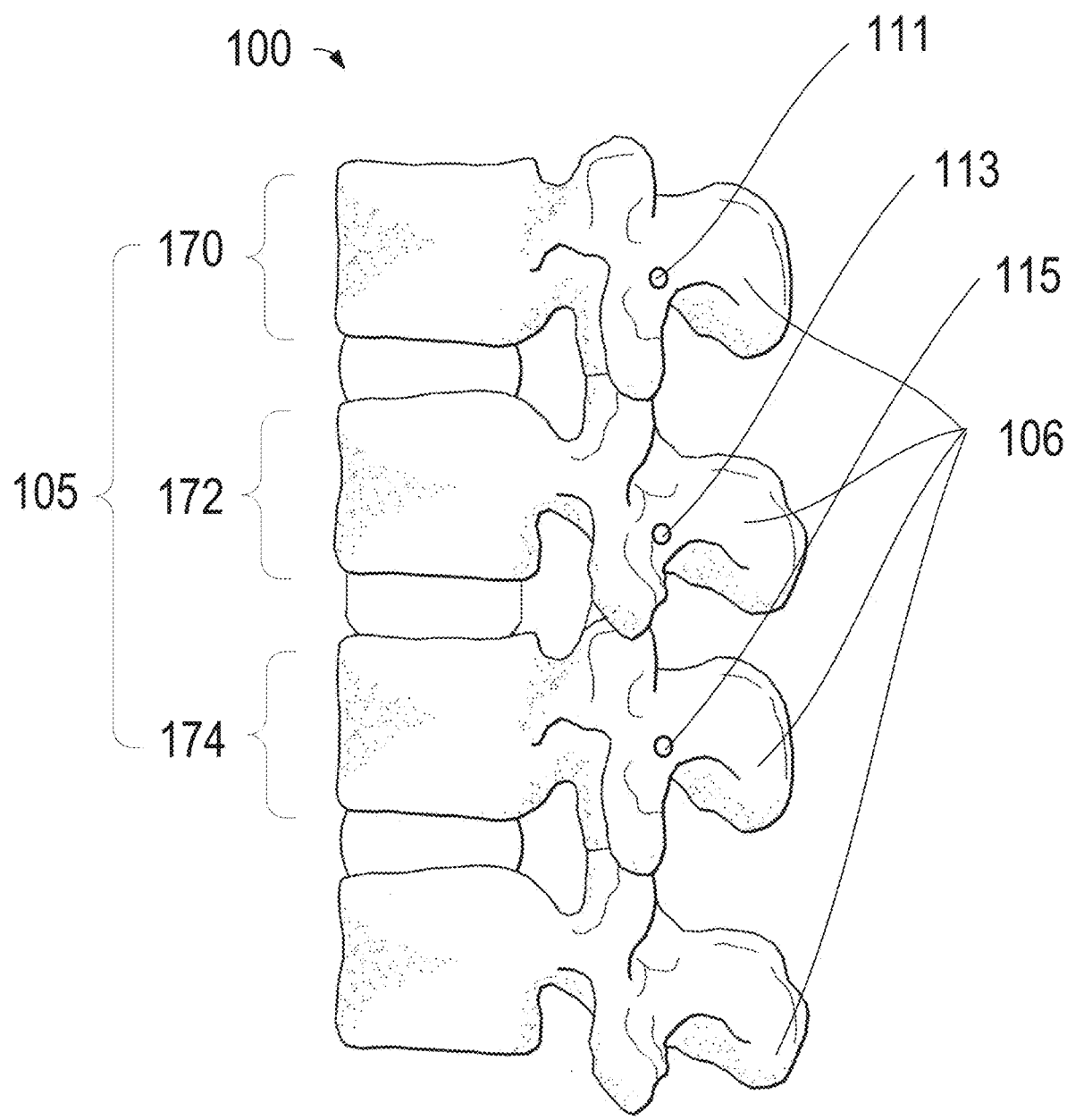
FIG. 4B describes a sagittal view of the vertebral column of FIG. 4A.

FIGS. 4A-B illustrate procedural steps of an embodiment of a method for holding one or more vertebrae together using one or more tension bands. Some components of the vertebral osteosynthesis equipment described above (e.g., vertebral osteosynthesis equipment 130, one or more connecting rods 132, one or more screws 134, one or more connectors 140) may not be shown in FIGS. 4A-B. However, it will be appreciated that one or more steps of the method described below may be conducted with one or more components of the vertebral osteosynthesis equipment (e.g., vertebral osteosynthesis equipment 130, one or more connecting rods 132, one or more screws 134, or one or more connectors 140).

Referring to FIGS. 4A-4B, transverse holes 111, 113 and 115 are made at or near the bases of the spinous processes 104 (e.g., preferably not the laminae) of the vertebrae of a patient, though the particular location isn't limiting. The transverse holes 111 113 and 115 are configured for receiving the tension bands therethrough. Alternatively, a grommet/ring/liner may be secured to one or more of the spinous processes, for receiving the tension band therethrough. The grommet may be provided with one or more attachment structures such as a first flange for securing to the spinous process. In one embodiment, a second flange is also provided, spaced apart from the first flange to receive the spinous process there between. A locking pin such as a bone screw or other connector may be utilized to secure the opposing first and second flanges through the spinous process and thereby secure the ring to the bone.

Although the vertebrae 170, 172, and 174 are referred to as top, middle, and bottom vertebrae, it will be appreciated that the vertebrae 172 and 174 may be two vertebrae on which the connecting rods 132 are mounted, and the vertebra 170 is a UIV+1 vertebra without the connecting rods 132 and most adjacent to the two vertebrae 172 and 174 on which the connecting rods 132 are mounted.

The transverse holes through the spinous process may be formed (e.g., drilled, punched, created) with the aid of a drill guide. The drill guide may guide the drill bit to a point which is approximately centered on the spinous process in the inferior-superior direction. The drill guide may also guide the drill bit to a point adjacent the base of the spinous process.

The edges of the drilled bore may be sufficiently rough to inhibit feeding the free end of the tension band there through. A drill bore liner, having a lumen defined by a tubular wall, may be placed within the bore to facilitate threading the end of the band therethrough. The liner may remain in the bore after threading the band, or may be removed. In some embodiments, the liner is biodegradable. The tubular wall may be provided with a radially outwardly extending annular flange, to seat against the side of the spinous process and retain the liner in position. Alternatively, a temporary tool such as a funnel shaped guide on a handle may be provided, to facilitate introduction of the tension band into the bore.

Figure 5:
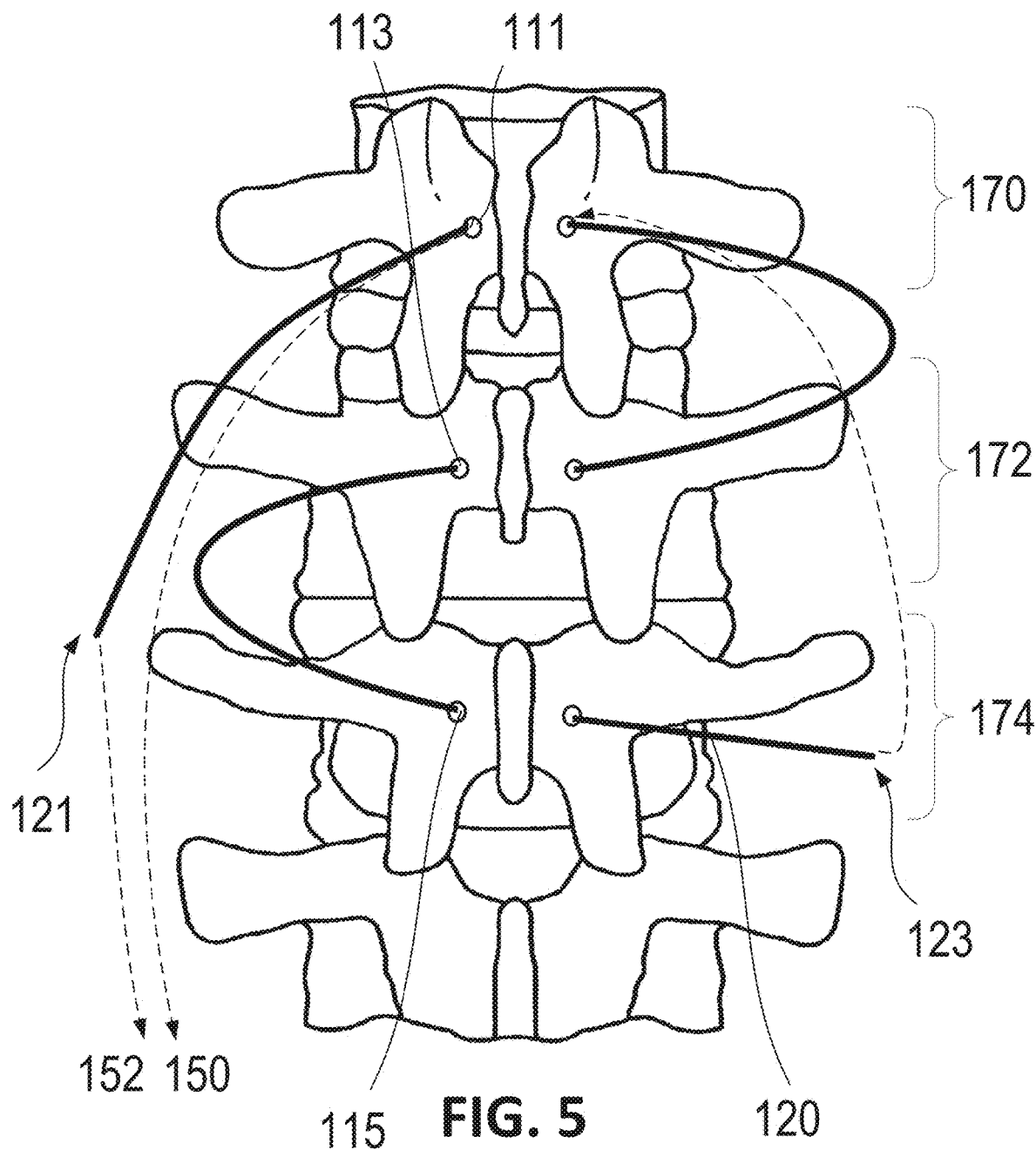
FIG. 5 illustrates a posterior view of a vertebral column illustrating an embodiment of a method or system explained herein.
Figure 6A:
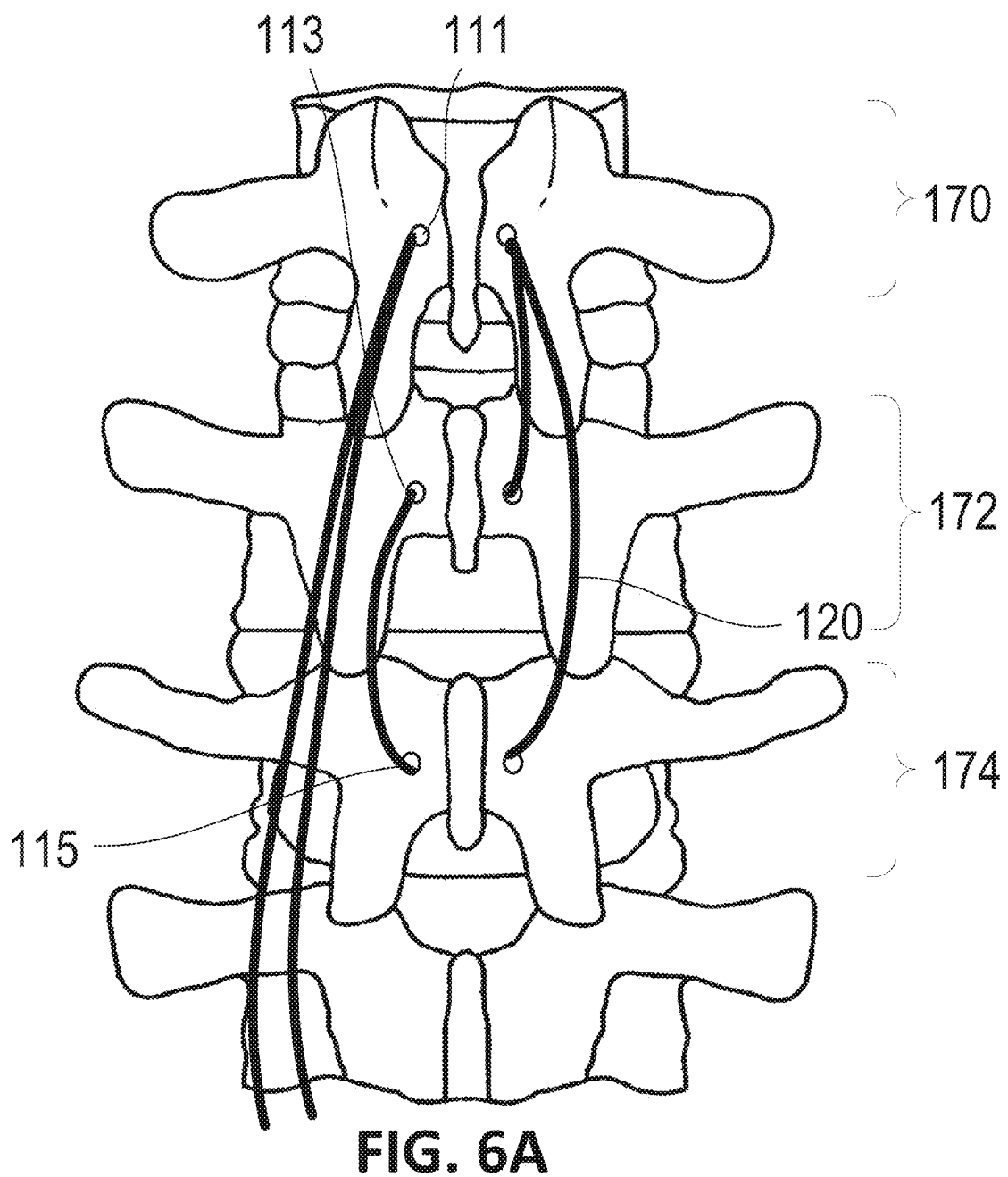
FIG. 6A illustrates a posterior view of a vertebral column describing an embodiment of a method or system explained herein.
Figure 6B:
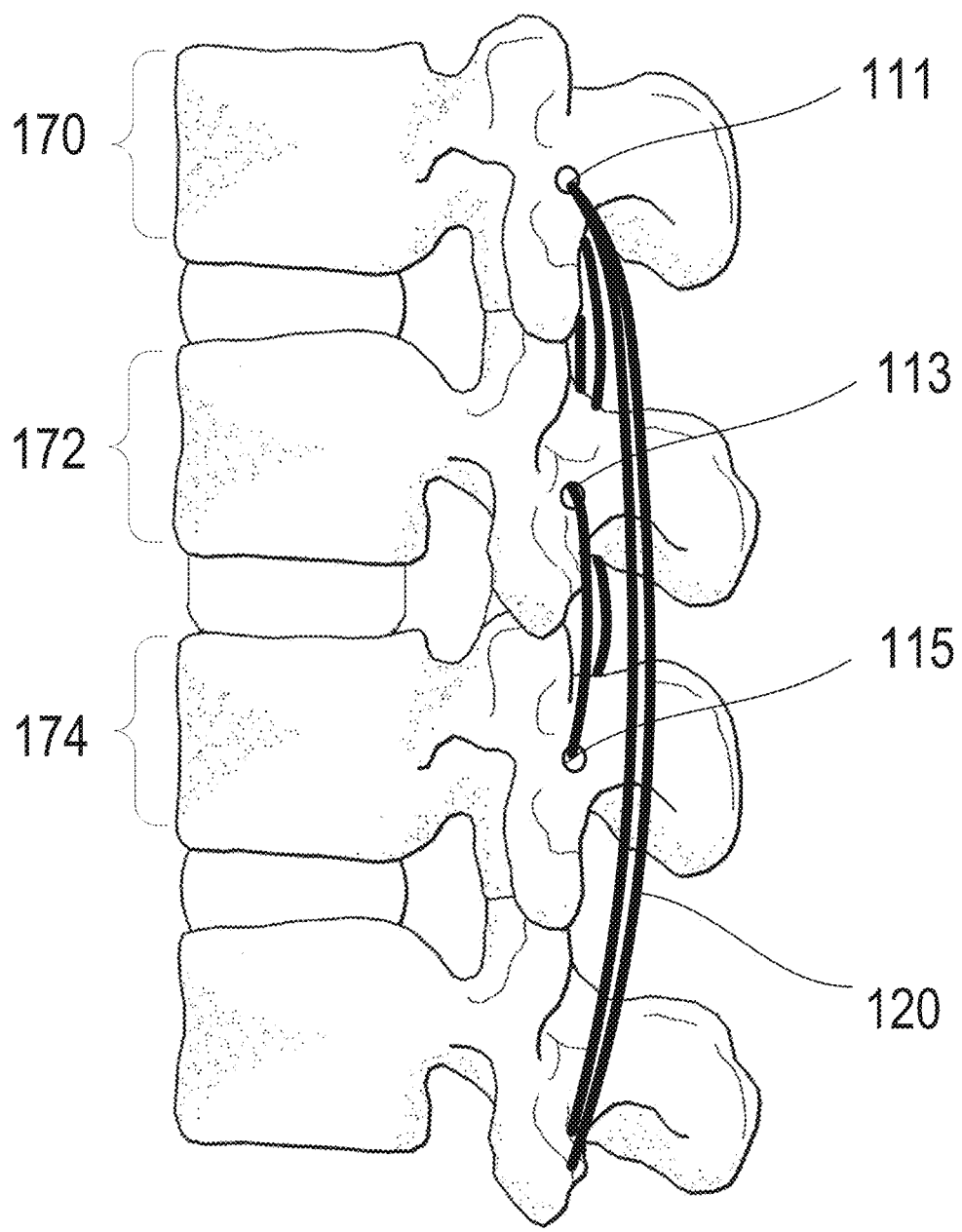
FIG. 6B shows a sagittal view of the vertebral column of FIG. 6A.

As shown in FIG. 5, a first tension band 120 can be installed in the vertebrae 170, 172, and 174 by passing a first end 121 of the tension band 120 through the hole 113 from left to right, through the hole 111 from right to left and then inferiorly in the direction of the corresponding connector. A second end 123 of the tension band 120 may be passed through the hole 115 from left to right and then through hole 111 from right to left and then inferiorly in the direction of the connector as shown in FIGS. 6A and 6B. That way, both ends 121, 123 of the tension band 120 extend out of the hole 111. Both ends of the tension band 120 may be pulled downward as shown by arrows 150 and 152 and secured under tension. FIGS. 6A and 6B illustrate posterior and sagittal views, respectively, of the tension band 120 installed in the vertebrae 170, 172, and 174 after steps described above.

In some embodiments, the tension band may thread past the UIV+1/−1. Thus, the tension bands may extend to UIV+2/−2, UIV+3/−3, etc. In some embodiments, the tension bands may equally extend from UIV (e.g., extend between +2/−2). In alternate embodiments, the tension bands may extend unequally from UIV (e.g., extend between +2/−3).

In some embodiments, vertebrae may be skipped. For example, vertebrae may be skipped if anatomy does not allow band passage. Thus, the tension bands may extend through UIV+1/−1 and move directly to UIV+3/−3. In some embodiments, if a vertebrae is skipped on the + side of UIV, the equivalent UIV—may be skipped as well. In some embodiments, the tension bands may equally extend from UIV. In alternate embodiments, the tension bands may extend unequally from UIV. In some embodiments, the tension bands may extend through the same vertebrae on the positive side of UIV and the negative side of UIV. In some embodiments, the tension bands may extend through different vertebrae on the positive side of UIV as compared to the negative side of UIV.

Figure 7:
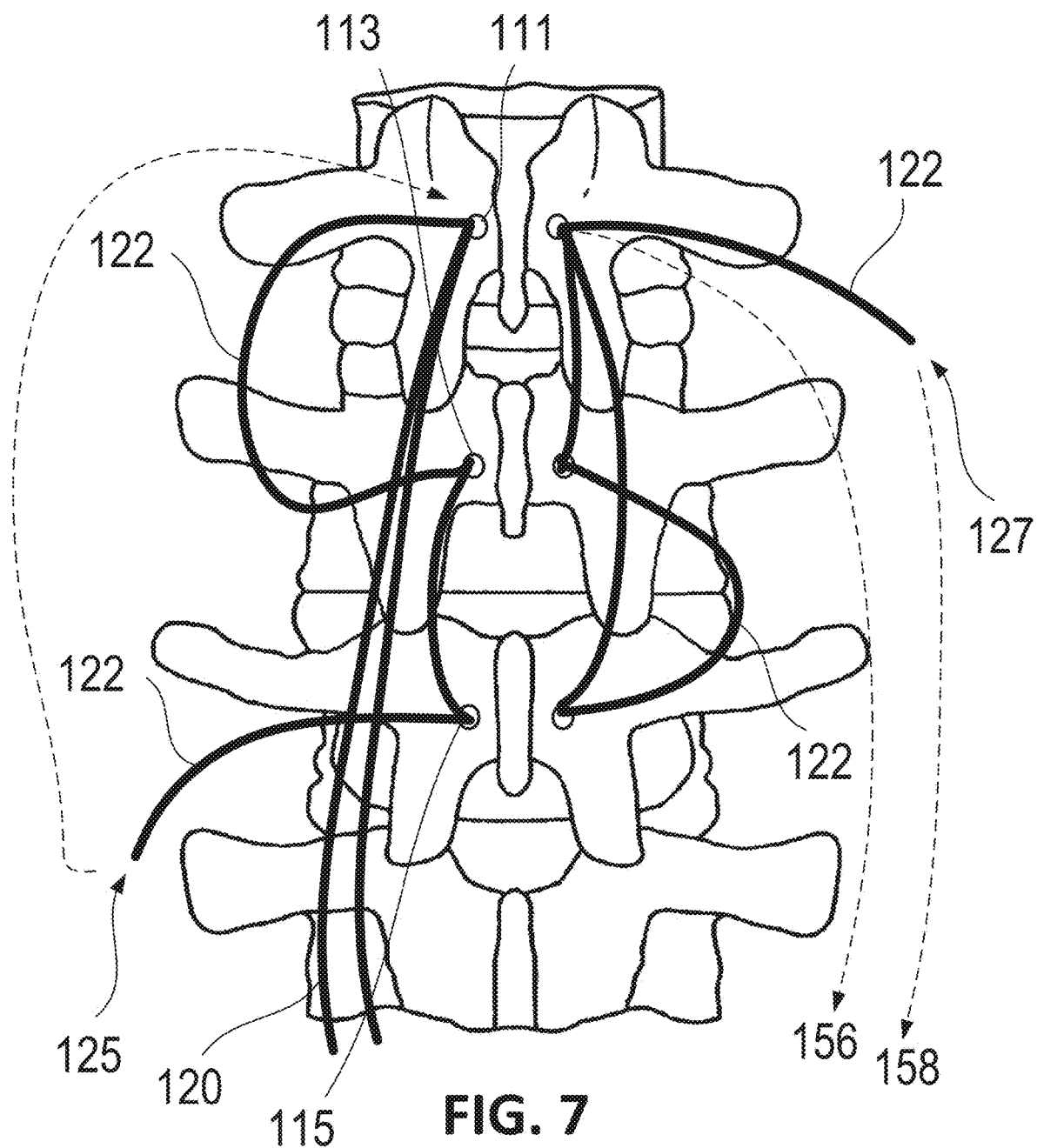

Referring to FIGS. 7 and 8, a second tension band 122 is installed in the vertebrae 170, 172, and 174 in a mirror image configuration. A first end 125 of the tension band 122 is passed through the hole 115 and directed towards the connector. A second end 127 of the second tension band 122 may be passed through the hole 113 from right to left, and then through the hole 111 and from left to right. That way, both ends 125, 127 of the tension band 122 exit the same side of hole 111. Both ends 125, 127 of the tension band 120 may be pulled downward as shown by arrows 156 and 158 in FIG. 7. FIG. 8 illustrates a posterior view of the tension bands 120 and 122 installed in the vertebrae 170, 172, and 174 after steps described above. It will be appreciated that steps described in FIGS. 5-6B may occur before, after, or simultaneous with those described in FIGS. 7-8. FIGS. 19A-19E illustrate additional views of the two tension band methodology. As shown, one of the tension bands can be attached to a left rod and the other can be attached to the right rod. In some embodiments, the tension band can be attached to rods directly, or to existing portions of the instrumentation or the patient's vertebrae.

While the above discloses one method for installing tension bands, it will be understood that other methods could be used as well. For example, ends of the tension band could be adhered within the holes in the vertebrae, and thus the tension band may only have one free end for applying tension. In some embodiments, the tension band could be chemically (e.g., glued, cemented, epoxied) or mechanically adhered within the holes in the vertebrae. In some embodiments, the tension band could be attached directly to the vertebrae. In some embodiments, the tension band could be connected with an intermediate component that can fit within the holes in the vertebrae, and the intermediate component can be attached to the vertebrae.

FIGS. 20A-B illustrate example methods for a single tension band 120 which can be used as an alternative to the dual tension bands discussed above. FIG. 20A illustrates a dual passage approach, where the tension band 120 may be looped through each of the holes 111/113/115 twice. As shown, moving from the right connector to the left connector, the band 120 may pass through hole 111 from right to left, through hole 113 from left to right, back through hole 111 from right to left, back through hole 113 from left to right, through hole 115 from right to left, back through hole 113 from left to right, through hole 115 from right to left, back through hole 113 from left to right, and back through hole 111 from right to left before attaching to a left connector.

Alternatively, a single passage approach can be used as shown in FIG. 20B. As shown, starting from the right connector, the band 120 can pass through hole 111 from right to left, through hole 113 from left to right, through hole 115 from right to left, back through hole 113 from left to right, and back through hole 111 from right to left before connecting to the left connector.

Different loop configurations can be used as well, and the described methodology is not so limiting. In some embodiments, the holes 111/113/115 can include separate lumens for each time the band 120 passes through the lumens. In some embodiments, the band may enter the same lumen multiple times.

In some embodiments, one end of the tension band 120 may connected to a left rod and the other to a right rod, for example through the connectors discussed herein.

In some embodiments, one or more of the tension bands can be re-tensioned after a period of time. For example, re-tensioning can occur every month, six months, one year, or two years. This can be done automatically, such as having the connector be configured to be rotated, such as through the use of an electrical connection, or manually through surgery. In some embodiments, the tension bands can be replaced after a period of time. In some embodiments, the tension bands will never have to be re-tensioned or replaced.

Figure 15:
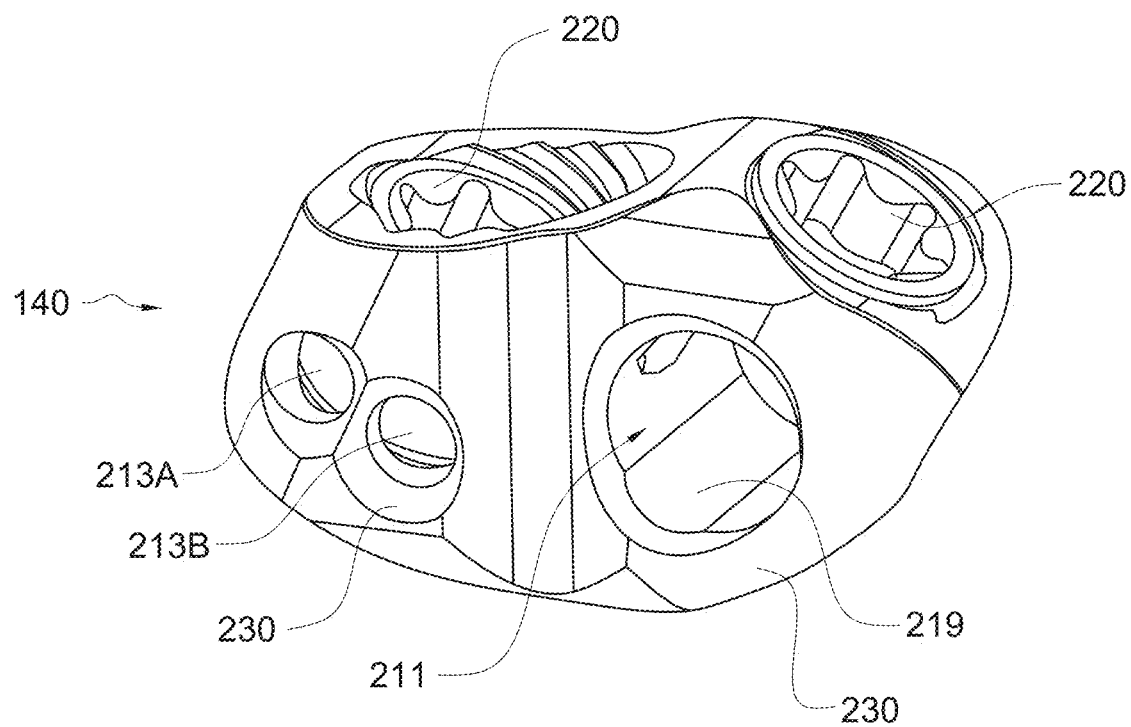
FIG. 15 is a perspective view of a modified connector.
Figure 16:
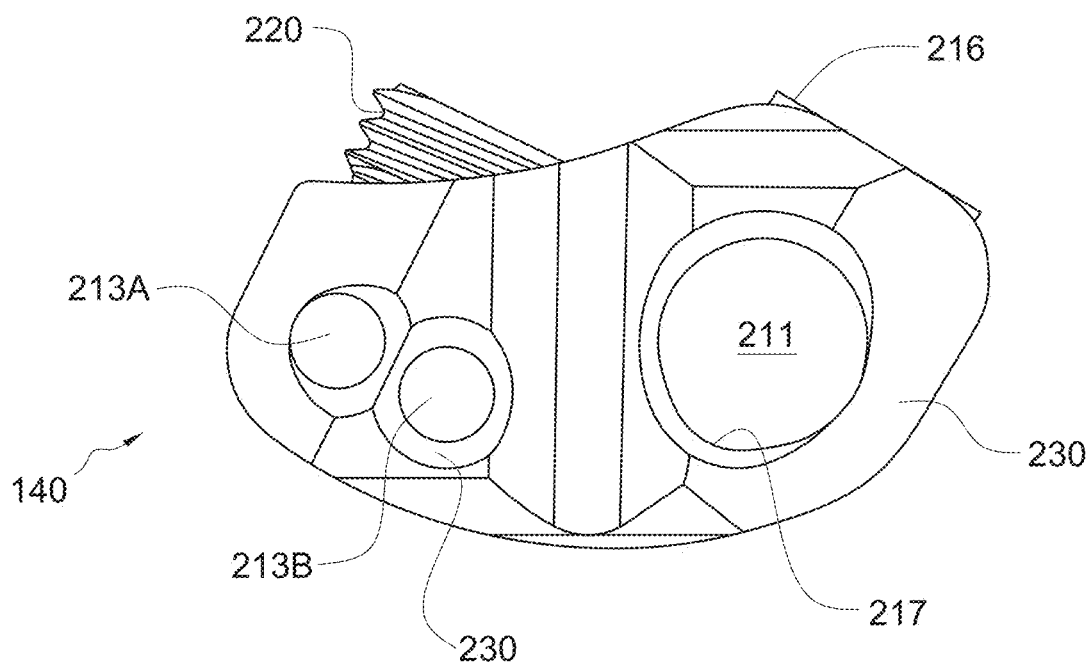
FIG. 16 is a side elevational view of the connector of FIG. 15.

Alternate connectors 140 are illustrated in FIGS. 15-18. Referring to FIG. 15, connector 140 includes a first locking interface such as conduit 211, for receiving a rod there through. A locking screw 216 is aligned to lock the rod into a longitudinal recess 217 as has been discussed.

At least one tension band conduit 213, and preferably a first tension band conduit 213A and a second tension band conduit 213B are provided for receiving the two inferiorly extending free ends of the tension band. At least one and preferably both openings of each tension band conduit 213A and 213B are provided with a tapered opening 230 to facilitate threading a free end of the tension band there through.

In the illustrated embodiment, a single locking screw 220 is configured to compress both tension band ends, extending through respective conduits 213A and 213B. Alternatively, a separate locking screw 220A and 220B (not illustrated) may be provided for each of the tension band conduits 213A and 213B respectively.

Each of the tension band conduits 213A and 213B, and the rod conduit 211 has a central longitudinal axis. All three of the central longitudinal axes extend approximately in parallel to each other, and preferably deviate from parallel by no more than about 15°, no more than about 10°, and in many embodiments no more than about 5° or 2° so that when mounted on a rod, the longitudinal axis of the tension band conduits extend in a generally inferior-superior direction in alignment with the inferiorly extending ends of the tension bands following exit from the spinous process aperture. The connector may be attached to the rod such that the tension band conduits are on the medial side of the rod, to allow the tension bands to provide a downward and medial bias on the connected spinous processes. In an embodiment (not illustrated) configured to lock to a cross bar, the longitudinal axes of the conduit 211 may be modified accordingly, but the longitudinal axes of the tension band conduits will preferably maintain the inferior-superior orientation to avoid bending the tension band.

Figure 17:
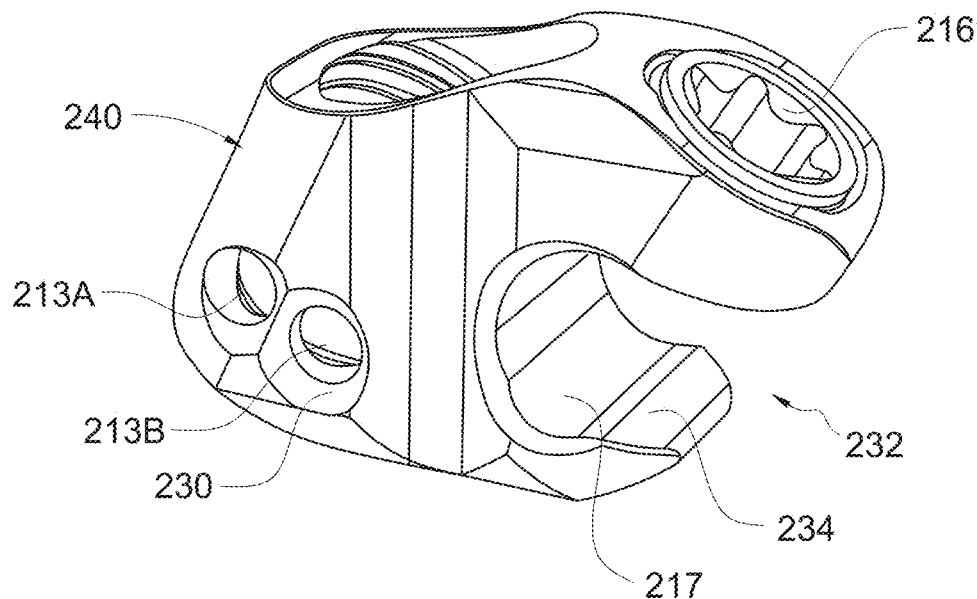
FIG. 17 is a perspective view of a further modification to the connector.
Figure 18:
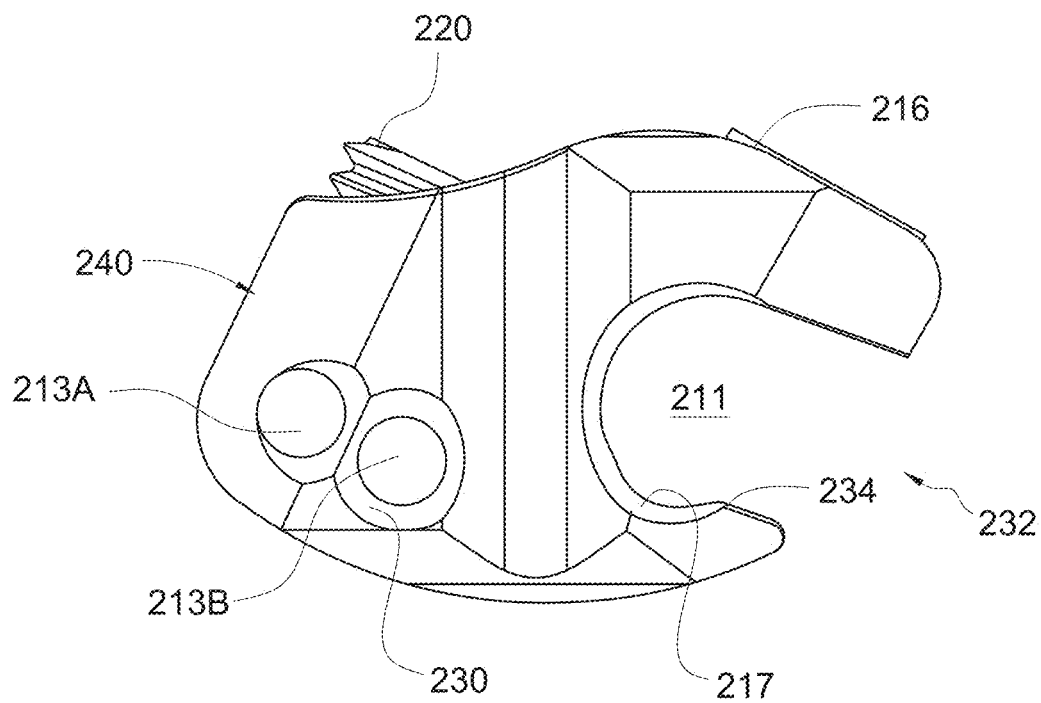
FIG. 18 is a side elevational view of the connector FIG. 17.
Figure 19E:
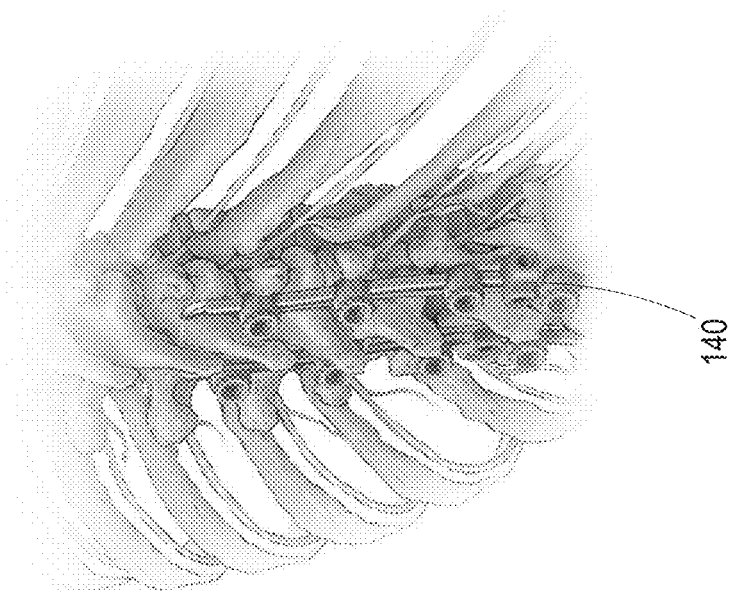
FIGS. 19A-19E illustrates an embodiment of a method of installing two tension bands into a vertebral column.
Figure 19B:
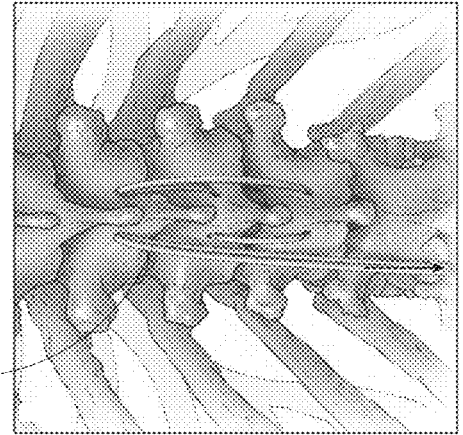
Figure 19D:
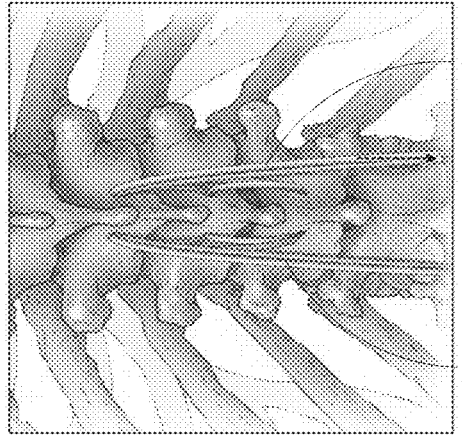
Figure 19A:
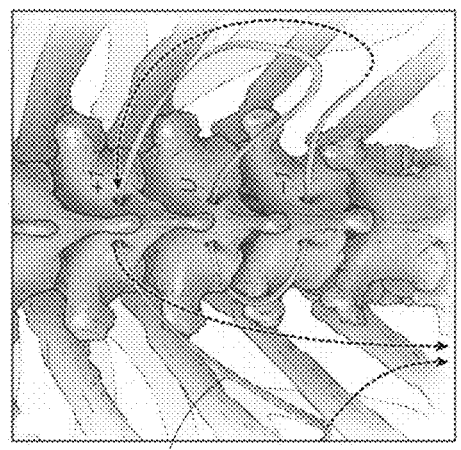
Figure 19C:
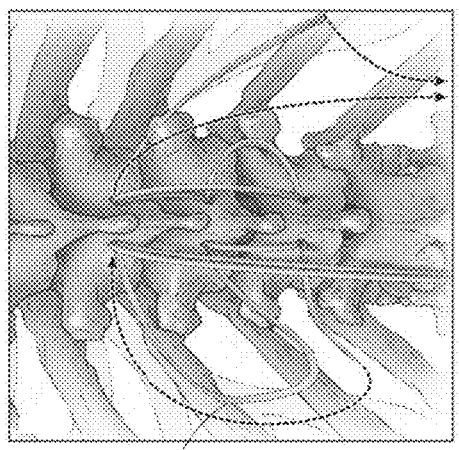

FIGS. 17 and 18 illustrate alternate connectors 240. Connector 240 can include any of the features discussed above with respect to the connectors 140 FIGS. 3A-3C and FIGS. 15-16. Connector 240 can also include additional unique features.

For example, the direction of the tension band conduits 213A/213B can be cranio caudal. Additionally, the connector 240 can have a dual independent locking mechanism for the rods and the bands.

Further, in the side mounting embodiment, a lateral opening 232 is provided in the sidewall 230, to allow the connector 240 to be advanced laterally onto the rod. This allows the surgeon to position the device on the rod once the construct is in place.

A circumferentially extending projection from the body such as an axially extending lip 234 is located adjacent longitudinal recess 217, to enable the rod to be entrapped within longitudinal recess 217 by distal advance of the locking screw 216. This construct enables attachment of the connector 240 after the rod has been fully secured to one or more bones screws to complete the posterior instrumentation.

Punching

FIGS. 9-13 illustrate embodiments of distal ends of a pliers type instrument (e.g., punch, punch instrument, pin, pin instrument) 300 configured for providing "punches" to create holes in the vertebrae as discussed above. Accordingly, the instruments 300 can allow a surgeon to punch a hole through the spinous process. The functional part (e.g., distal end) shown in the figures can include two components, male 302 and female 304, working together to punch through the bone. The punch can form different shaped holes (e.g., round, oval, square, triangular), and the particular shape is not limiting. Generally, the punch instrument may include two pivotably connected arms 306 which are connected proximal to functional distal ends. For example, the arms can be pivotably connected similarly to scissors or forceps.

Figure 10:
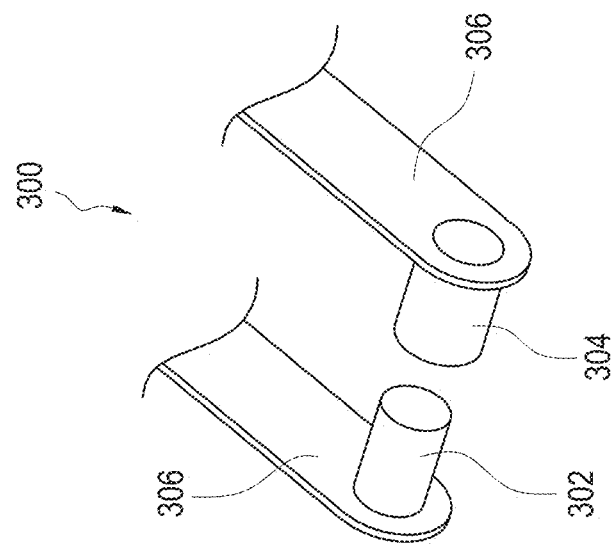
Figure 9:
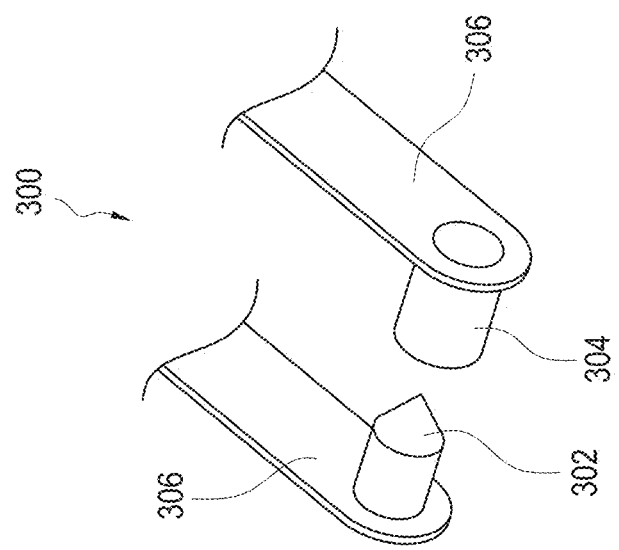

As shown in FIG. 9, in some embodiments the punch instrument 300 where the male component 302 can be solid. The male component 302 can abut the female component 304 in the closed position to provide the punch. As shown, the male component 302 can be tapered/pointed or have a sharp point/edge for cutting through bone. In some embodiments, the male and female components 302/304 may be hollow, such as shown in FIG. 10. The female component 304 may have a greater diameter than the male component 302, and thus the male component 302 can fit within the female component 304 in the closed position.

FIG. 11 illustrates an embodiment of a punch instrument 300 positioned at a spinous process. The male component 302 can be solid and the female component 304 can be, for example, hollow, in order to receive the male component 302 in the closed position. Both components 302/304 penetrate the bone 310 to create the punch hole. In this implementation, a tubular female component 304 could be detachable to remain in the bone and serve as a liner or grommet to isolate the bone structures when the tension band in introduced. In some embodiments, the female component 304 is not detachable.

FIG. 12 illustrates an embodiment of a punch instrument 300 where again the male component 302 is a solid component and the female component 304 is hollow. As compared to FIG. 11, this embodiment shows a shorter female component 304. Thus, in this embodiment, only the male component 302 penetrates the bone 310 to create the punch hole. The female component 304 is intended to penetrate the bone 310 only superficially in order to stabilize the instrument and avoid the instrument 300 from slipping.

FIG. 13 illustrates an embodiment of a punch instrument 300 in which the male component 302 is hollow and long enough to extend at least about 80% or 90% or entirely the width of the spinous process 310, and the female component 304 is hollow and short. Only the male component 302 penetrates the bone 310 to create the punch hole. The female component 304 is intended to penetrate the bone 310 superficially in order to avoid the instrument from slipping. The band can be introduced through the hollow male component 302 which may be detachable to form a tubular bore liner.

Figure 14:
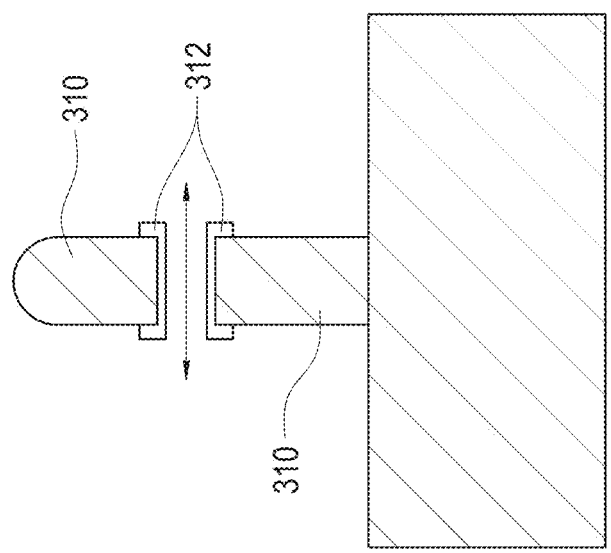
FIG. 14 illustrates an embodiment of a grommet in position.

FIG. 14 illustrates an embodiment of a grommet 312 in position in bone 310, which may have been deployed from a conventional pliers type grommet tool, or by the hole punch described herein. As shown, the grommet 312 can remain within the vertebrae after forming the punch. The grommet 312 can be useful for creating a smoother or rougher surface for extending the tension band through. Further, as shown, the grommet 312 can extend over edges of the hole, reducing any sharp surface there. Thus, it may prevent the band from catching or breaking during application/tension.

Accordingly, there are a number of options to introduce the tension band through the spinous process. For example, the tension band can extend directly through the bone, or through a grommet 312 such as discussed above. The grommet can be incorporated into the punching instrument so that the grommet 312 remains after punching, or can be introduced after the punch hole is formed.

System Kit

The above-described equipment/components can be included in a kit. The equipment may be contained within a container, such as a bag, box, etc., or may be separate and loose. The kit can include, for example, one or more tension bands (e.g., 1, 2, 3, 4, 5, 6, 7, 8, 9, or 10) and one or more of any of the connectors discussed above (e.g., 1, 2, 3, 4, 5, 6, 7, 8, 9, or 10). The connectors can all be the same, or there can be a variety of connectors. The kit can further include liners, bone punches, or grommets as discussed above. No particular equipment is required, and some kits may include more or less equipment. In some embodiments, alcohol swabs, betadine, cloth, or other equipment can further be included, and the discussion herein should not be so limited.

Implementing Systems and Terminology

Implementations disclosed herein provide systems, methods and apparatus for limiting flexion of vertebrae and/or inhibiting adjacent level kyphosis or adjacent level failure by way of a vertebral osteosynthesis equipment comprising a tension band.

As used herein, "distal" refers to the end of a tool positioned closest to the patient during use, and "proximal" refers to the end of a tool positioned closest to the operator (e.g., a physician). Stated differently, the relative positions of components of a tool are described herein from the vantage point of the operator.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

From the foregoing description, it will be appreciated that inventive tensioning systems, kits, and methods of use are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

The disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A method of inhibiting proximal junctional failure in a patient having posterior spinal instrumentation, comprising the steps of:
    creating a first transverse bore through a spinous process of a vertebral body of a spine, superior and adjacent an uppermost instrumented vertebral body, a second transverse bore through a spinous process of the uppermost instrumented vertebral body, and a third transverse bore through a spinous process of a vertebral body inferior and adjacent the uppermost instrumented vertebral body;
    threading a tension band having a first end and a second end through the first, second and third bores;
    extending the tension band inferiorly of the third transverse bore, under tension; and
    locking the tension band with respect to the spine.

2. The method of claim 1, wherein the locking comprises attaching a connector to the posterior spinal instrumentation and locking the tension band to the connector.

3. The method of claim 1, wherein the locking comprises attaching a connector to the spine and locking the tension band to the connector.

4. The method of claim 1, wherein the tension band has first and second ends, and both the first and second ends exit the first transverse bore and are locked under tension to a connector secured with respect to the spine.

5. The method of claim 4, wherein the posterior spinal instrumentation includes a left rod and a right rod, and the tension band is secured to the connector at a point that is medial to the left and right rods.

6. The method of claim 1, wherein the creating a first transverse bore step comprises locating opposing jaws of a bone punch on opposing sides of the spinous process, and punching the first transverse bore.

7. The method of claim 1, further comprising inserting a liner into at least the first transverse bore, prior to the threading a tension band step.

8. The method of claim 7, wherein the inserting the liner comprises inserting a grommet into at least the first transverse bore.

9. The method of claim 1, wherein the tension band extends through the first bore in a first direction, the second bore in a second direction generally opposite the first direction, and the third bore in the first direction, wherein the first end of the tension band is located one a first side of the spinous process and where the second end of the tension band is located on a second side of the spinous process.

10. The method of claim 9, wherein the second end of the tension band extends through the first bore in the first direction.

11. The method of claim 10, wherein the method further comprises extending a second tension band having a first end and a second end through the first bore, the second bore, and the third bore.

12. The method of claim 11, wherein the second tension band extends through the first bore in the second direction, the second bore in the first direction, and the third bore in the second direction, wherein the first end of the second tension band is located on the second side of the spinous process and the first end of the second tension band is located on the first side of the spinous process.

13. The method of claim 12, wherein the second end of the second tension bands extends through the first bore in the second direction.

* * * * *